(12) United States Patent
Buechler

(10) Patent No.: US 6,670,196 B1
(45) Date of Patent: Dec. 30, 2003

(54) RAPID EVALUATION OF THE RATIO OF BIOLOGICAL MOLECULES

(75) Inventor: Kenneth F. Buechler, San Diego, CA (US)

(73) Assignee: Biosite, Inc., San Diego, CA (US)

( * ) Notice: Subject to any disclaimer, the term of this patent is extended or adjusted under 35 U.S.C. 154(b) by 0 days.

(21) Appl. No.: 09/081,722

(22) Filed: May 13, 1998

Related U.S. Application Data

(60) Provisional application No. 60/046,467, filed on May 14, 1997, and provisional application No. 60/047,081, filed on May 19, 1997.

(51) Int. Cl.[7] .................. G01N 33/543; G01N 33/48; C12P 21/04
(52) U.S. Cl. .................. 436/518; 435/7.1; 435/7.21; 435/7.24; 435/7.94; 435/810; 435/975; 436/63; 436/69; 436/501; 436/527; 436/533; 436/822; 422/56; 422/57; 422/68.1; 530/463; 530/807
(58) Field of Search .................. 435/7.1, 7.21, 435/7.24, 7.92, 7.94, 810, 970, 975; 436/63, 69, 527, 533, 501, 503, 518, 548, 813, 822, 807; 422/56, 57, 68.1; 530/403, 807

(56) References Cited

U.S. PATENT DOCUMENTS

| | | | |
|---|---|---|---|
| 3,817,837 A | | 6/1974 | Rubenstein et al. |
| 3,935,074 A | | 1/1976 | Rubenstein et al. .. 195/103.5 R |
| 4,690,890 A | * | 9/1987 | Loor et al. .................. 435/7 |
| 4,737,453 A | * | 4/1988 | Primus .................. 435/5 |
| 4,806,468 A | | 2/1989 | Wagner et al. .................. 435/7 |
| 5,196,309 A | * | 3/1993 | Ginsberg .................. 435/7.21 |
| 5,480,792 A | | 1/1996 | Buechler et al. .................. 435/6 |
| 5,501,983 A | * | 3/1996 | Lilja et al. .................. 436/518 |
| 5,529,902 A | | 6/1996 | Kottke et al. .................. 435/7.21 |
| 5,599,677 A | * | 2/1997 | Dowell et al. .................. 435/7.4 |
| 5,763,199 A | * | 6/1998 | Coller .................. 435/7.21 |
| 5,985,579 A | * | 11/1999 | Buechler et al. .................. 435/7.1 |

FOREIGN PATENT DOCUMENTS

| | | |
|---|---|---|
| EP | 0 378 391 A2 | 7/1990 |
| GB | 2 206 411 A | 5/1989 |
| WO | 94/24559 | 10/1994 |
| WO | 95/06877 | 3/1995 |
| WO | 96/10749 | 4/1996 |
| WO | 96/33415 | 10/1996 |

OTHER PUBLICATIONS

Woods et al., Autoantibodies Against the Platelet Glycoprotein IIb/IIIa Complex in Patients With Chronic ITP, Blood 63(2): 368–375 (1984).*

Adams, et al., "Comparable Detection of Acute Myocardial Infarction by Creatine Kinase MB Isoenzyme and Cardiac Troponin," *Clin. Chem.* 40, 1291–1295 (1994).

Bhayana, et al., "Discordance Between Results for Serum Troponin T and Troponin I in Renal Disease," *Clin. Chem.* 41, 312–317 (1995).

Henderson, et al., "CEDIA, a New Homogeneous Immunoassay System," *Clin. Chem. 32,* 1637–1641 (1986).

Katus et al., "Diagnostic Efficiency of Troponin T Measurements in Acute Myocardial Infarction," *Circulation 83,* 902–912 (1991).

Olefsky, "Diabetes Mellitus," *Cecil Textbook of Medicine,* 18th Edition, 2:1360–1381 (1988).

* cited by examiner

*Primary Examiner*—Long V. Le
*Assistant Examiner*—Changhwa J. Cheu
(74) *Attorney, Agent, or Firm*—Foley & Lardner; Richard J. Warburg

(57) ABSTRACT

The invention relates in part to novel methods of rapidly determining the ratio of biological molecules. The invention also relates in part to a kit for rapidly determining the ratio of biological molecules.

28 Claims, 4 Drawing Sheets

RAPID EVALUATION OF THE RATIO OF BIOLOGICAL MOLECULES

RELATED APPLICATIONS

The present document claims priority to U.S. Provisional Application Serial No. 60/046,467, filed May 14, 1997, as well as U.S. Provisional Application Serial No. 60/047,081, filed May 19, 1997, both of which are incorporated herein by reference in their entirety, including any figures, tables, and drawings.

BACKGROUND

The following description of the background of the invention is provided to aid in understanding the invention, but is not admitted to be or describe prior art to the invention.

Existing methods for determining ratios of biological molecules involve multiple steps and often require a large amount of time to perform. These methods often utilize two or more components, usually antibodies, specific for each of the biological molecules. Thus, two or more discrete assays need to be conducted to determine the ratio. Hence, these systems prolong the time required to determine the ratio and also accumulate reagent costs.

In addition, many of the existing methods for determining the concentrations of biological molecules utilize several components, usually antibodies or labeled antigens, at concentrations in excess of the concentration of the biological molecules in a sample. Non-competitive or sandwich assays function by the use of antibodies in excess of the biological molecules. Competitive immunoassays function through a competition of binding of a biological molecule and a labeled biological molecule for a limited concentration of antibody. Because some biological molecules, such as hemoglobin or cell receptors, occur at high concentrations in biological fluids, existing methods that require components to be in excess of the biological molecules are of limited application. In addition, samples generally require a dilution prior to assay.

Determining the ratio of biological molecules has proved to be an important indicator for many medical conditions and procedures. In particular, the determination of the ratio of related biological molecules is useful. Related biological molecules are formed in an organism when a biological molecule becomes modified. Biological molecules can become modified, for example, by covalent chemical alteration or by the reversible binding of molecules.

Biological molecules can become chemically modified in an organism in an intermolecular fashion. For example, hemoglobin, a blood-borne oxygen carrier in organisms, can become modified by glucose moieties when the blood stream contains high levels of glucose. In the blood stream, the aldehyde group of glucose condenses with valine of hemoglobin to form a Schiff base. This reversible reaction is followed by a virtually irreversible rearrangement in which the double bond shifts to C-2 of the sugar to give a stable fructose derivative of hemoglobin. Stryer, *Biochemistry*, 3rd Ed., W. H. Freeman and Co., New York 1988. Hemoglobin that is modified in this manner is referred to as hemoglobin A1-C.

In addition, biological molecules can be modified in an intramolecular fashion. For example, troponin I, which normally exists in a reduced form in muscle cells, is oxidized when it is released into the blood stream of organisms suffering from a myocardial infarction. In particular, cysteine moieties within a discrete troponin I molecule can oxidize to form an intramolecular disulfide linkage. Methods of detecting related forms of troponin I that are released from muscle cells after a myocardial infarction are disclosed in PCT publication WO 96/33415.

Biological molecules can also become reversibly modified when high-affinity ligands bind to them. Cell receptors, for example, which are presented on the surface of a cell, can bind natural ligands or synthetic ligands with equilibrium dissociation constants in the micromolar to picomolar range.

SUMMARY

The invention relates in part to novel methods of rapidly determining the ratio of biological molecules. The invention also relates in part to a kit for determining the ratio of related biological molecules.

The invention increases the rate for determining ratios of biological molecules as compared to the rates of determining these ratios using existing methods. The invention increases the rate for determining ratios of biological molecules by reducing the number of steps required for measuring the ratio.

Applicant has discovered that the ratio of biological molecules can be rapidly detected without measuring the absolute concentrations of the biological molecules by using a binding molecule, preferably an antibody, that recognizes each of the biological molecules but binds only one of the biological molecules at a time.

FIG. 1, which depicts one embodiment of the invention, serves as an illustrative example for the rapid determination of the ratio of biological molecules. The number of steps are reduced by probing a sample with a first component that binds a fraction of each of the biological molecules of interest. When the concentration of the first component is less than the concentrations of the biological molecules, the first component binds the biological molecules in a ratio related to the ratio at which the biological molecules exist in solution.

In one embodiment, the binding of one of the biological molecules to the first component excludes the binding of the other, even though the first component has the capacity of binding each of the molecules independently. The distribution of the biological molecules bound to the first compound is a statistical distribution that is directly related to the distribution of biological molecules in the sample.

These two features of the first component, the multiple binding feature and the exclusive binding feature, allow the first component to bind the biological molecules in a ratio related to the ratio of the biological molecules in the sample. For example, if the first component can bind each of molecules A and B, and A and B exist in the sample at a 3 to 1 ratio, the bound first component will have bound A and B in a 3 to 1 ratio or nearly this ratio.

Biological molecules A and B bind to the first component in a ratio related to their ratio in the sample, the relative on rates of the A and B binding to the first component determining the final ratio of A and B bound to the first component. Thus, the ratio of A to B can be bound to the first component in a ratio that is proportional to the ratio of A to B existing in a sample.

The second component of the invention detects the complex formed between the first component and one of the biological molecules. This complex may be detected when the second component binds to only one of the biological molecules, e.g., A or B, or if the second component binds to the complex formed between one of the biological molecules and the first component. The latter instance may provide an advantage if the biological molecules exist at high concentrations in the sample with respect to the concentration of the second component, since the second component will bind the complex comprising one biological molecule and the first component and not the unbound biological molecule.

Once the second component binds the complex comprising the first component and a biological molecule, a signal can be measured from a reporter molecule linked to one of the components of the invention. This signal can be applied to a standard curve that relates the signal to a ratio of the biological molecules. The standard curve can be prepared by measuring the signal, by the methods described herein, for samples prepared with known ratios of the biological molecules.

When biological molecules do not bind to the first component with equal affinity, standard curves relating the ratio to a signal generated by one of the components, preferably the first component, can be utilized to determine the ratio of A to B in the sample. In addition, normalization factors can be utilized to determine the ratio of A to B in a sample.

The ratio of the biological molecules is determined most rapidly when the components and the sample are mixed together at the same time and in the same vessel. This approach minimizes the number of steps required to determine the ratio of biological molecules, and thereby represents an advantage over existing techniques for determining the ratio of biological molecules. In particular, applications of the methods and kits described herein relate in part to increasing the efficiency of monitoring drug delivery, monitoring the historic blood-glucose level in diabetic patients, and monitoring the time of myocardial infarction.

The rapid rate of determining the ratio of biological molecules can enhance the recovery of patients suffering from particular medical conditions. Proper treatment can be expedited since the diagnosis results can be determined in a rapid manner. In the case of heart attacks, for example, a rapid determination of the oxidized to reduced troponin I ratio will hasten the determination of the time of a myocardial infarction, and thereby expedite the administration of a proper treatment to the patient. Expediting the treatment of a patient will improve that patient's recovery from the myocardial infarction.

The rapid rate of determining the ratio of related biological molecules can also enhance the delivery of a therapeutic drug to a patient. In the case of a drug that binds and blocks a cell surface receptor, a rapid determination of the free receptor to occupied receptor ratio can determine whether a larger or smaller dose of the drug should be delivered to the patient for an effective therapy.

Furthermore, the invention allows for the determination of ratios of related biological molecules that exist at high concentrations in a sample. Hemoglobin, for example, exists at high concentrations in a patient's blood stream. Hemoglobin becomes hemoglobin A1-C when it is modified with glucose in the patient's blood stream. One component of the invention can isolate a fraction of the total hemoglobin molecules (hemoglobin and hemoglobin A1-C) and a second component can isolate one of the related molecules (such as hemoglobin A1-C) to determine the ratio of these related molecules even when they exist at high concentrations in a sample. This application of the methods described herein is useful for diabetic patients since hemoglobin A1-C represents the average blood glucose concentration over periods of time longer than one day. Because diabetic patients often cannot accurately determine their blood glucose levels due to variable readings using the techniques currently available to them, the methods and kits of the invention provide for the accurate and rapid determination of the average blood glucose level for diabetic patients.

Thus in a first aspect, the invention features a method of determining a solution ratio of biological molecules. The method comprises the steps of: (a) contacting the biological molecules with (i) a first component having specific binding affinity to each biological molecule, where the biological molecules bind to the first component in a binding ratio related to the solution ratio of the biological molecules; (ii) contacting the biological molecules with a second component having specific binding affinity for one of the biological molecules; and (b) determining the amount of a complex comprising the biological molecule, the first component, and the second component present as a measure of the solution ratio.

The term "biological molecules" as used herein refers to two or more molecules that exist naturally or unnaturally in a biological organism or fluid or an environmental sample. The ratio is preferably measured for four or more biological molecules, more preferably measured for three biological molecules, and most preferably measured for two biological molecules. The biological molecules can be related or unrelated. Biological molecules can be related by virtue of modification of one of the biological molecules. Thus, related molecules can exist as an unmodified molecule and a modified molecule.

A biological molecule may be modified in at least two manners: (i) modified covalently in an intermolecular or intramolecular fashion, or (ii) modified reversibly with a high affinity molecule. The molecule may be modified covalently by the addition of another chemical moiety (i.e., hemoglobin modified by a glucose moiety). An example of a molecule modified by a reversibly binding affinity molecule is a free receptor bound by an affinity ligand. The ligand may be a naturally occurring binding molecule of the free receptor or may alternatively be a synthetic ligand.

When the biological molecules of interest do not exist in a sample, the methods and kits of the invention can determine that the biological molecules do not exist in the sample. These types of results often yield useful information. For example, a determination that a blood sample contains negligible amounts of oxidized troponin I, might indicate that the patient from which the blood sample was taken has not suffered myocardial infarction. This type of result could save a hospital and patient from making large expenditures on health care for a condition which never existed. Thus, even when the methods of the present invention yield a negative result, the results monitored by the methods and kits of the invention are useful.

Examples of biological molecules include, but are not limited to organic and inorganic molecules, drugs, peptides, nucleic acids, receptors, cells and proteins.

The term "receptor" as used herein refers to a nonprotein or a protein component that binds specifically or nonspecifically to a molecule. Examples of receptors include, but are not limited to cell surface receptors, antibodies, binding proteins, binding fragments, avidin, non-protein templates and biomimetic receptors.

The term "component" as used herein refers to a molecule that specifically binds to one or more of the biological molecules. The component preferably comprises a protein or polypeptide or peptide, more preferably comprises a peptidomimetic or organic compound, and most preferably comprises an antibody.

The term peptidomimetic as used herein refers to a peptide-like molecule containing non-hydrolyzable chemical moieties in place of one or more hydrolyzable moieties existing in naturally occurring peptides. Thus, regions of a peptide which are hydrolyzable, such as carboxyl moieties, are replaced by non-hydrolyzable moieties, such as methylene moieties, in a peptidomimetic.

The term "antibody" as used herein refers to a monoclonal antibody, a polyclonal antibody, a binding fragment of an antibody, and a recombinant antibody. The term "antibody" also refers to a receptor protein that can specifically bind to a target.

The terms "specific binding affinity" or "specifically binds" or "specifically bound" as used herein describe a component of the invention, preferably comprising, consisting of, or consisting essentially of an antibody, that binds to one or more biological molecules with greater affinity than it binds to other molecules under specified conditions. For instance, a first component of the invention may comprise a binding moiety having specific binding affinity for hemoglobin and hemoglobin A1-C; the binding moiety will not appreciably bind to molecules that are not hemoglobin or hemoglobin A1-C. Preferably, a component of the invention binds to a molecule with a specific binding affinity at least 5 times greater than it binds to other molecules, more preferably 10 times or 50 times greater than it binds to other molecules, and most preferably 100 times greater than it binds to other molecules.

The term "binding moiety" as used herein refers to a molecule that comprises a component of the invention having specific binding affinity for a biological molecule or biological molecule/first component complex. The binding moiety is preferably a protein, polypeptide, or peptide, more preferably a peptidomimetic or organic compound, and most preferably an antibody.

Methods of binding and determining the amount of antibodies bound to a target in a sample are well-known to those skilled in the art. Harlo & Lane, *Antibodies, A Laboratory Manual,* 1989, Cold Spring Harbor Laboratories. The components that bind to the biological molecules of the invention can be monitored using techniques known to those skilled in the art. These techniques include manual applications and applications involving mechanical and electronic instrumentation.

The first component of the invention can bind to the biological molecules in a binding ratio related to the solution ratio of the biological molecules. The term "related" refers to solution ratios and binding ratios that are equal or nearly equal to one another. The solution ratio and binding ratio are nearly equal to one another when the ratio of the solution ratio to the binding ratio is between 0.1 and 10, preferably between 0.2 and 5, more preferably between 0.5 and 2, and most preferably equal to 1.

The solution ratio is also related to the binding ratio of the biological molecules when (i) one of the biological molecules can bind to the first component at one time, and (ii) each biological molecule has a similar on rate and a similar equilibrium constant for binding the first component. Thus, the binding of one of the biological molecules excludes the binding of another biological molecule also having specific binding affinity to the first component. This feature of the invention allows the first component to bind the biological molecules of interest in the same or related ratio as the molecules exist in the sample being probed with the components of the invention. These conditions allow the binding ratio to be of the same or related value to the solution ratio.

The term "complex" as used herein refers to two or more discrete molecules bound to one another in a non-covalent manner. Thus, a complex, for example, can comprise a biological molecule bound to a first component of the invention. The complex may also consist of or consist essentially of the first component bound to one biological molecule. In addition, a complex may exist that comprises, consists of, or consists essentially of a biological molecule and a first component. Furthermore, a complex may exist that comprises, consists of, or consists essentially of a biological molecule, a first component, and a second component. If the first component comprises an antibody, the first component may form a complex comprising, consisting of, or consisting essentially of the first component and two distinct types of biological molecules, due to the dual binding capacity of antibodies. Similarly, if the first component is an antibody, the first component may form a complex comprising, consisting of, or consisting essentially of the first component, two distinct types of biological molecules, and a second component. An antibody may also bind two molecules of the same type of biological molecule. Thus the complexes may contain two molecules of the same type of biological molecule.

A complex may be stable with respect to dilution of the free molecules comprising the complex when the molecules comprising the complex bind to one another with high affinity. High affinity interactions between the molecules of the complex can be achieved by noncovalent interactions, for example, such as electrostatic interactions, hydrophobic interactions, Van der Waals interactions, and hydrogen bond interactions.

The term "amount" as used herein refers to an indication of the presence of a complex comprising, consisting of, or consisting essentially of a biological molecule, a first component, and a second component. The amount may be expressed, for example, in terms of an absorbance change or a change in fluorescent emission measured at one or more wavelengths in the ultraviolet, visible, or infrared range of wavelengths. An optical density or a fluorescent reading may be calculated into a ratio using a standard curve of the invention, as described herein by example. The amount can be assessed directly from a signal generated from one of the components themselves or by a separate component that specifically binds to the complex, which comprises, consists of, or consists essentially of a biological molecule, a first component, and a second component.

The term "ratio" as used herein refers to the fraction of biological molecules. The ratio, for example, may represent the fraction of modified molecule to unmodified molecule. The ratio of these biological molecules may be expressed by the following fractions:

[unmodified molecule]/[modified molecule];
[modified molecule]/[unmodified molecule];
[unmodified molecule]/[modified molecule+unmodified molecule]; and
[modified molecule]/[modified molecule+unmodified molecule].

The ratio may also be determined for multiple biological molecules. For example a ratio might be determined for one biological molecule A to three other biological molecules B C, and D. This ratio could be determined by using a first component that binds to each of A, B, C, and D, where the binding of any one of A, B, C, or D excludes the binding of any of the others. The second component would have specific binding affinity for A. The ratio could be expressed as:

$[A]/[B+C+D]$ or $[A]/[A+B+C+D]$.

Likewise, the ratio of biological molecule B to the biological molecules A, C, and D can be measured using a second component having specific binding affinity for B. The ratio for this relation can be expressed as:

$[B]/[A+C+D]$ or $[B]/[A+B+C+D]$

In general, the ratio of two or more biological molecules can be determined using the novel teachings described herein.

The term "solution ratio" as used herein refers to the ratio of the biological molecules as they exist in solution. The solution ratio may be the same ratio or a different ratio than the ratio of the biological molecules bound to the first component.

The term "binding ratio" as used herein refers to the ratio of the biological molecules bound to the first component of the invention. The biological molecules may bind to the first component in the same or different ratios as they exist in the sample. Therefore, the binding ratio of the biological molecules may be the same or different than the solution ratio of the biological molecules.

The solution ratio is similar to the binding ratio of the biological molecules where (i) one of the biological molecules can bind to the first component at one time, and (ii) the biological molecules bind to the first component with a similar on rate and a similar equilibrium constant for binding the first component. Thus, the binding of one of the biological molecules excludes the binding of another biological molecule also having specific binding affinity to the first component.

The term "similar equilibrium constant" refers to equilibrium dissociation constants for the first molecule binding to each of the biological molecules within a five-fold difference with respect to one another. This feature of the invention allows the first component to bind the biological molecules of interest in the same or different ratios as the molecules exist in the sample being probed with the components of the invention. These conditions allow the binding ratio to be of the same or similar value to the solution ratio.

In a preferred embodiment, one or more components 30 may have specific binding affinity for an epitope that consists of, or consists essentially of, a portion of a biological molecule and a portion of another component. For example, in FIG. 1A, the second component may have specific binding affinity for a portion of molecule B and a portion of component 1. This example also applies to FIGS. 1B and 1C. Examples of components, such as antibodies, that have specific binding affinity for an epitope that consists of a binding interface for two other molecules are well known in the art.

The term "epitope" as used herein can refer to a surface to which a component of the invention has specific binding affinity. An epitope can be a portion of a molecule of any size. An epitope can also be a portion of one molecule and a portion of one other molecule, where the two molecules bind to one another in a complex. An epitope on such a complex can consist of a region of one molecule and a region of another molecule that are adjacent and are located at a binding interface of the two molecules.

In another preferred embodiment the invention relates to the method of determining the ratio of biological molecules where the method further comprises one or more other distinct first components having specific binding affinity to other distinct biological molecules. By utilizing multiple distinct first components, the invention provides for a method of determining two or more ratios of biological molecules. For example, one first component can be utilized to measure the ratio of biological molecules A and B in a sample, and in the same sample, a different first component can determine the ratio of biological molecules C and D. This example can be readily modified by a person of ordinary skill in the art to include measuring multiple ratios of biological molecules using multiple first components of the invention.

In another preferred embodiment the invention relates to the method of determining the ratio of biological molecules, where the method further comprises one or more other distinct second components each having specific binding affinity for distinct biological molecules. Each distinct second component has specific binding affinity for only one biological molecule. Multiple second components can be utilized in conjunction with either one first component or multiple first components. An example of the former application is provided herein by example with respect to measuring ratios of biological molecules important for thrombosis. An illustration of using multiple second components in conjunction with one first component is presented in FIG. 1D. A protocol that entails the utilization of one first component in conjunction with two or three second components is provided herein by example. An illustration of utilizing multiple second components in conjunction with multiple first components is presented in FIG. 1C.

When the ratio of three or more biological molecules is measured using only one first component, the solution ratio and binding ratios are nearly equal to one another when the ratio of the solution ratio to the binding ratio is between 0.1 and 10, preferably between 0.2 and 5, more preferably between 0.5 and 2, and most preferably equal to 1.

In a preferred embodiment, the invention relates to the method of determining the ratio of biological molecules, where at least one of the components comprises an antibody. In this preferred embodiment, the first component can comprise an antibody, the second component can comprise an antibody, or the first component and the second component can comprise antibodies. Thus, the method can utilize a first component that comprises an antibody and a second component that comprises another type of polypeptide or organic molecule. Alternatively, the method may relate to two components that comprise antibodies.

In yet another preferred embodiment, the invention relates to the method of determining the ratio of biological molecules, where at least one of the components comprises a reporter molecule. In this preferred embodiment, the first component can comprise a reporter molecule, the second component can comprise a reporter molecule, or the first component and the second component can comprise reporter molecules. If both components comprise reporter molecules, the reporter molecules may be the same types of molecules, or preferably, different types of reporter molecules.

The term "reporter molecule" as used herein refers to a signal generator or a signal generating element. These terms can refer to a number of elements: enzymes and their resultant effects on a substrate, colloidal metal particles, latex and silica particles with dye incorporated, and dye particles are examples of signal generators. An enzyme can catalyze the turnover of a substrate to produce a product that is detectable, for example, by absorbance or fluorescence technologies (e.g., ultra-violet, visible, infrared) or detectable by shift in pH. Reporter molecules may be linked to components of the invention, in particular antibodies, by techniques well-known to those skilled in the art. See e.g., Harlo & Lane, *Antibodies, a Laboratory Manual,* 198, Cold Spring Harbor Laboratories for examples of methods used to link reporter molecules to antibodies and other proteins as well as examples of various reporter molecules commonly used by those skilled in the art. The linkage can be a chemical moiety of varying length. The components of the invention may be modified with a reporter molecule either before the components are added to a sample comprising the biological molecules under study, or alternatively, after the components are added to the sample being probed with the components of the invention.

In another preferred embodiment the invention relates to the method of determining the ratio of biological molecules, where at least one component comprises a specific recognition moiety. In this preferred embodiment, the first component can comprise a specific recognition moiety, the second component can comprise a specific recognition moiety, or the first component and the second component can comprise specific recognition moieties. If both components comprise specific recognition moieties, the specific recognition moieties may be different from one another or the same recognition moiety.

The term "specific recognition moiety" as used herein refers to a molecule covalently linked to a component of the invention which can be recognized by another binding molecule. The specific recognition moiety can be a peptide, polypeptide, protein, or a non-peptide molecule. An example of such a specific recognition moiety is a peptide moiety originating from the hemagglutinin protein, which can bind commercially available antibodies with high affinity. The anti-hemagglutinin peptide antibody, or more generally, a binding moiety that can specifically bind to the specific recognition moiety, can exist free in solution or can be attached to a solid support.

The term "solid support" as used herein refers to a matrix composed of a material that does not dissolve in aqueous solutions. The solid support can be composed of such materials as carbohydrate and plastic materials. Many examples of commercially available solid supports are available to those skilled in the art. Examples of solid supports are latex and silica particles, plastics, agarose, cellulose, and polyethylene. Because solid supports with reactive chemical moieties present on their surfaces are commercially available or can be chemically synthesized using well known techniques in the art, components of the invention can be linked to the solid support either before or after the components are added to the sample comprising biological molecules under study. The components of the invention can be linked to the support either directly or by a spacer molecule. Examples of chemical linkages between solid supports and other molecules are well known to those skilled in the art (e.g., this information can be found in the Pierce catalogue). In addition, purified forms of biological molecules themselves can be linked to solid supports using techniques commonly known to those skilled in the art.

In another preferred embodiment the invention relates to the method of determining the ratio of biological molecules, where at least one of the components comprises a linkage to a solid support. In this preferred embodiment, the first component can comprise a linkage to a solid support, the second component can comprise a linkage to a solid support, or both the first and the second component can comprise linkages to solid supports. If both components comprise linkages to solid supports, the solid supports may be different types of solid supports, or are of the same type of solid support, but each type of component is linked to discrete solid support entities. The term "discrete solid support entities" as used herein refers to one component linked to one solid support and another type of component linked to another solid support, where the solid support composition may be the same or different.

In another preferred embodiment, the invention relates to the method of determining the ratio of biological molecules, where the second component has specific binding affinity for a complex comprising, consisting of, or consisting essentially of one biological molecule and the fist component. The invention is preferably practiced in the manner stated by this preferred embodiment when the concentration of the biological molecule exceeds the concentration of the second component to which that biological molecule specifically binds. The second component can bind a complex of two or more molecules when a binding region of the second component has specific binding affinity to a region on a biological molecule and an adjacent region on the first component. Examples of bifunctional organically synthesized molecules as well as antibodies that bind complexes exist in the art. See, e.g., U.S. application Ser. No. 08/071,203 filed Jun. 1, 1993, and U.S. application Ser. No. 08/458,901 filed Jun. 2, 1995.

In a preferred embodiment, the invention relates to the method of determining the ratio of biological molecules, where the first component comprises a binding moiety having specific binding affinity for each of the biological molecules of interest. Each of the molecules bind to the first component in a ratio related to their solution ratio. For example, a binding moiety may have specific binding affinity for a modified molecule and its related unmodified form: a binding moiety may have specific binding affinity for hemoglobin and its modified form, hemoglobin A1-C. The binding moiety may bind to the modified and unmodified forms of biological molecules with equal affinity or unequal affinity. If the two forms of the biological molecules bind to the first component with unequal affinity, a normalization factor can be determined to correct for the actual ratio of the biological molecules bound to the first component. Alternatively, the ratio can be simply determined using a standard curve constructed as described herein by example. It can be advantageous to select antibodies with unequal affinity to the biological molecules if it is preferred to preferentially bind one of the biological molecules. For example, a larger, dynamic range can be achieved when one biological molecule is one-half or less than the concentration of the other biological molecule.

In another preferred embodiment, the invention relates to the method of determining the ratio of biological molecules, where the first component comprises: (a) a first binding moiety having specific binding affinity for one biological molecule; and (b) a second binding moiety having specific binding affinity for another of the biological molecules of interest. In this preferred embodiment, the first component can bind each of the biological molecules of interest, but is constructed such that each of the biological molecules compete for it. Specifically, the first component may only bind to one of the biological molecules of interest at one time. The invention can also relate to a first component in which the first binding moiety has specific binding affinity for one biological molecule and a second binding moiety has specific binding affinity for one or more other biological molecules. In this manner, a ratio can be determined for one molecule to a family of molecules if desired. Preferably, the ratio is determined for one biological molecule to one other biological molecule.

In other preferred embodiments, the invention relates to the method of determining the ratio of biological molecules, where one or more of the binding moieties of the first component or second component are antibodies.

In yet another preferred embodiment the invention relates to the method of determining the ratio of biological molecules, where the biological molecules are occupied receptor and free receptor.

The term "free receptor" as used herein refers to a molecule that functions by binding another molecule. A free receptor is a receptor molecule that is unbound by a ligand. A receptor molecule can exist on the surface of a cell or within the cell. Examples of receptors found on the surface of cells are mitogenic receptors (such as epidermal growth factor receptor and platelet derived growth factor receptor), metabolic receptors (such as insulin receptor and transferrin receptor), platelet aggregation receptors (such as glycoprotein IIbIIIa receptor), steroid receptors, and hormone receptors.

The term "occupied receptor" as used herein refers to a receptor that is bound by a ligand. The term "ligand" refers to a molecule that binds to the receptor with high affinity. Examples of naturally occurring ligands of receptors are, for example, iron for the transferrin receptor, epidermal growth factor for the epidermal growth factor receptor, and fibrinogen or specific drugs, such as Reopro®, for binding to the glycoprotein IIbIIIa receptor. The ligand may also be a synthetic ligand which binds with high affinity to the receptor. The term "high affinity" as used herein in reference to a receptor-ligand interaction refers to a dissociation equilibrium binding constant between 1 $\mu$M and 0.01 pM.

An example of a pharmaceutically relevant free/occupied receptor system relates to receptor glycoprotein IIbIIIa and its role in thrombosis. Thrombosis is the process in which red blood cells form a clot upon binding fibrinogen. Various drugs already in the market or entering the market can bind to the glycoprotein IIbIIIa receptor and block the clotting process. Methods set forth herein can determine the amount of the anti-clotting drug required to effectively block the clotting process.

In yet another preferred embodiment, the invention relates to the method of determining the ratio of biological molecules, where the biological molecules are hemoglobin and hemoglobin A1-C.

The term "hemoglobin" as used herein refers to a protein molecule that transports oxygen in the blood of organisms. Hemoglobin exists at high concentrations in an organism's blood.

The term "hemoglobin A1-C" refers to hemoglobin that is modified when the-glucose concentration is high in an organism's blood stream. Hemoglobin is modified by glucose moieties when the concentration of glucose achieves a critical concentration in the bloodstream of an organism. Hemoglobin is glycosylated at higher levels in diabetic patients as compared to non-diabetic patients because diabetic patients' blood contain abnormally high concentrations of glucose.

In another preferred embodiment, the invention relates to the method of determining the ratio of biological molecules, where the biological molecules are oxidized troponin I and reduced troponin I.

The term "reduced troponin I" as used herein refers to troponin I containing two cysteine moieties that are capable of undergoing intramolecular oxidation. The cysteine amino acids have side chains of formula —$CH_2$—SH. Reduced troponin I can contain at least two cysteine residues. Components of the invention can be specific for the reduced form of troponin I since it exists in a different protein conformation than the oxidized form of troponin I.

The term "oxidized troponin I" as used herein refers to troponin I containing one or more cystine moieties in an oxidized form. Oxidized cystine amino acids have side chains of formula —$CH_2$—$S^-$. Oxidized troponin I can contain at least one cystine residue that is in an oxidized form.

In yet another preferred embodiment, the invention relates to the method of determining the ratio of biological molecules where the first component is specific for both occupied receptor and free receptor, and where the second component is specific for: (a) occupied receptor; (b) free receptor; (c) a complex comprising, consisting essentially of, or consisting of occupied receptor and the first component; or (d) a complex comprising, consisting essentially of, or consisting of free receptor and the first component. As described herein, the free receptor may relate to glycoprotein IIbIIIa and the occupied receptor may relate to glycoprotein IIbIIIa bound to a drug.

The term "specific for both occupied receptor and free receptor" as used herein refers to a component, preferably an antibody, of the invention that can bind to a receptor or to a component comprising the receptor whether or not it is free or occupied. This type of component does not discriminate against free or occupied receptor. This component, however, binds to a receptor with higher affinity than to other molecules.

The first component, which binds to both the free and occupied forms of receptor, is different than the second component, which specifically binds to one of the forms of the receptor in an unbound state or a bound state or one of the forms of the receptor in a complex with the first component. A second component that specifically binds to a complex comprising, consisting of, or consisting essentially of free receptor and the first component, for example, will not specifically bind to a complex comprising, consisting of, or consisting essentially of occupied receptor and the first component.

In another preferred embodiment, the invention relates to the method of determining the ratio of biological molecules, where the first component is specific for both hemoglobin and hemoglobin A1-C, and where the second component is specific for: (a) hemoglobin; (b) hemoglobin A1-C; (c) a complex comprising, consisting essentially of, or consisting of hemoglobin and the first component; or (d) a complex comprising, consisting essentially of, or consisting of hemoglobin A1-C and the first component.

The term "specific for both hemoglobin and hemoglobin A1-C" as used herein refers to a component, preferably an antibody, of the invention that combines to hemoglobin whether or not it is modified by glucose. or unmodified by glucose. This type of component does not discriminate against hemoglobin that is not modified by glucose and hemoglobin that is modified by glucose. This component, however, binds to hemoglobin with higher affinity than to other proteins.

A first component that specifically binds to both hemoglobin and hemoglobin A1-C is different than a second component that specifically binds a complex comprising, consisting of, or consisting essentially of hemoglobin A1-C and the first component. In addition, a second component that specifically binds a complex comprising, consisting of, or consisting essentially of hemoglobin and the first component, for example, will not specifically bind to a complex comprising, consisting of, or consisting essentially of hemoglobin A1-C and the first component.

In yet another preferred embodiment the invention relates to the method of determining the ratio of biological molecules, where the first component is specific for both oxidized troponin I and reduced troponin I and where the second component is specific for: (a) oxidized troponin I; (b) reduced troponin I; (c) a complex comprising, consisting essentially of, or consisting of oxidized troponin I and the first component; or (d) a complex comprising, consisting essentially of, or consisting of reduced troponin I and the first component.

The term "specific for both oxidized troponin I and reduced troponin I" as used herein refers to a component, preferably an antibody, of the invention that binds to troponin I whether or not it is oxidized or reduced. This type of component does not discriminate against oxidized or reduced troponin I. This component, however, binds to troponin I with higher affinity than to other proteins.

A first component that specifically binds to both oxidized and reduced troponin I is different than a second component that specifically binds a complex comprising, consisting of, or consisting essentially of oxidized troponin I and the first component. In addition, a second component that specifically binds a complex comprising, consisting of, or consisting essentially of oxidized troponin I and the first component, for example, will not specifically bind to a complex comprising, consisting of, or consisting essentially of reduced troponin I and the first component.

In another preferred embodiment the invention relates to a method of determining the ratio of biological molecules, further comprising the step of contacting the biological molecules with a third component. The third component is preferably added to a sample comprising the biological molecules after the first and second components have been added to the sample, but added before the free molecules are washed away or before the ratio of the biological molecules is determined. The third component has specific binding affinity for a complex comprising the first biological molecule and the second component.

The third component can bind to a complex comprising the first biological molecule and the second component when the third component binds adjacent regions located on the first biological molecule and the second component.

In yet another preferred embodiment the invention relates to a method of determining the ratio of biological molecules, where the third component comprises a specific recognition moiety. This specific recognition moiety can be utilized to bind the complex to a solid support. Examples of specific recognition moieties are disclosed herein. The specific recognition moiety linked to the third component can be the same moiety as the specific recognition moiety potentially linked to the second component, but is preferably a different moiety than the recognition moiety potentially linked to the second component.

In another preferred embodiment, the invention relates to the method of determining the ratio of biological molecules, further comprising the step of removing molecules that are not bound to the complex comprising a biological molecule, a first component, and a second component before determining the amount of this complex.

The term "removing" as used herein refers to a method of separating molecules from those existing in a complex comprising, consisting of, or consisting essentially of a biological molecule, a first component, and a second component. This method can be accomplished by attaching the first or the second component to a solid support and washing away molecules that are not bound to either the first or second component. These techniques are well-known to those skilled in the art. See e.g., Harlo and Lane, *Antibodies, a Laboratory Manual,* 1989, Cold Spring Harbor Laboratories.

A person of ordinary skill in the art could readily adapt the concepts and components of the invention to a method that does not require a solid support. Homogeneous assay methods have been described in the art where the amount of a given biological molecule can be determined by the change in the fluorescence polarization of a component to which the biological molecule binds. Some homogeneous assay techniques applicable to this invention are described in WO94/24559, U.S. Pat. Nos. 3,817,837 and 3,935,074, and in *Clin. Chem.* 32, 1637–1641, (1986) incorporated herein by reference in their entirety including any references and diagrams. Thus, changes in the physical parameters of the components of the invention (e.g., fluorescence polarization or absorbance or wavelength) could be monitored when biological molecules bind to them. These changes in physical parameters can be used to directly determine the ratio of biological molecules without the use of a solid support.

In another preferred embodiment, the invention relates to the method of determining the ratio of biological molecules further comprising the step of comparing the amount of the complex comprising a biological molecule, a first component, and a second component to a standard curve, where the standard curve relates the amount of this complex to the ratio of the biological molecules. This complex could further comprise a third component, where the third component has specific binding affinity for a complex comprising the first biological molecule and the second component. In addition, the third component can comprise a specific recognition moiety.

The term "standard curve" as used herein refers to a measured relationship between the ratio of biological molecules to the amount of the complex comprising a biological molecule, a first component, and a second component. This complex could further comprise a third component, where the third component has specific binding affinity for a complex comprising the first biological molecule and the second component. In addition, the third component can comprise a specific recognition moiety. The amount of the complex can be quantified by a signal generated by a reporter molecule linked to one of the components of the invention. The relationship between the ratio and the signal in a standard curve, for example, may be linear or obey a non-linear function. The standard curve can be generated by measuring the signal generated by the methods of the invention for samples containing known ratios of biological molecules. These methods are described by example herein.

The term "signal" as used herein refers to a spectroscopic or chemical change caused by a reporter molecule attached to either a component of the invention or another component used to detect a complex comprising a biological molecule, a first component, and a second component. As described herein, the signal can, for example, take the form of a fluorescence emission, a change in the wavelength of a fluorescence emission, an absorbance measurement, a change in infrared wavelength, or a change in the pH of the solution.

The term "comparing" as used herein, in reference to a standard curve, refers to extrapolating the ratio of biological molecules from a standard curve by using the amount of the second component bound to the biological molecules of interest. Because the standard curve relates the ratio of biological molecules to the signal generated by the method of the invention, applying a signal measurement to the standard curve can generate an estimated ratio of the biological molecules.

In another preferred embodiment, the invention relates to the method of determining the ratio of biological molecules, further comprising the step of comparing the signal generated from a reporter molecule to a standard curve. The standard curve can relate the amount of the reporter molecule to the ratio of the biological molecules.

In another aspect, the invention relates to a method for determining one or more solution ratios of three or more biological molecules. This method for determining the solution ratios of one or more biological molecules comprises the steps of: (a) contacting the biological molecules with (i) a first component having specific binding affinity for each of the biological molecules, where the biological molecules bind to the first component in a binding ratio related to the solution ratio of the biological molecules; (ii) a second component having specific binding affinity for a first biological molecule of the biological molecules; (iii) a different second component having specific binding affinity for a second biological molecule of the biological molecules; and (b) determining the amount of a complex comprising the first biological molecule, the first component, and the second component or the amount of a complex comprising the second biological molecule, the first component, and the different second component as a measure of the solution ratio.

In a preferred embodiment the invention relates to the method of determining the ratios of three or more biological molecules, wherein at least one of the components comprises an antibody.

In another preferred embodiment the invention relates to the method of determining the ratios of three or more biological molecules, wherein at least one of the components comprises a specific recognition moiety.

In yet another preferred embodiment the invention relates to the method of determining the ratios of three or more biological molecules, wherein at least one of the components comprises a linkage to a solid support.

In another preferred embodiment the invention relates to the method of determining the ratios of three or more biological molecules, wherein at least one of the components comprises a reporter molecule.

In yet another preferred embodiment the invention relates to the method of determining the ratios of three or more biological molecules, where the biological molecules are activated platelets, free glycoprotein IIbIIIa receptor, occupied glycoprotein IIbIIIa receptor, and P-selectin.

The term "activated platelets" as used herein refers to biological process of forming a thrombis. Inactive platelets and activated platelets express the protein glycophorin on the cell surface. Inactive platelets also express free glycoprotein IIbIIIa receptor. This receptor can bind fibrinogen, which activates the platelets and induces them to form a thrombis. Activated platelets, but not inactive platelets, express the protein P-selectin on the cell surface. Molecules that bind and occupy the glycoprotein IIbIIIa receptor can block the binding of fibrinogen to the receptor and thereby inhibit the activation of platelets and inhibit the formation of thrombis clots. The methods provided herein by example an determine the ratio of occupied to free glycoprotein IIbIIIa receptor and the ratio of activated to inactive platelets.

The term "inactive platelets" as used herein refers to platelets that have the potential to be activated but have not yet been activated because the proper activation signal has not activated them or because a drug is bound to the glycoprotein IIbIIIa receptor and blocking the activation signal.

The term "free glycoprotein IIbIIIa receptor" as used herein refers to the receptor that is not bound by fibrinogen or by any drug molecules.

The term "occupied glycoprotein IIbIIIa receptor" as used herein refers to the receptor that is bound by fibrinogen or by drug molecules which inhibit the activation of platelets.

The term "glycophorin" as used herein refers to a protein that is expressed on the surface of both inactive and activated platelets.

The term "P-selectin" as used herein refers to a protein that is expressed on the surface of activated platelets.

In other preferred embodiments the invention relates to the method for determining the ratio of three or more biological molecules, where the amount of the complex comprising the first biological molecule, the first component, and the second component is a measure of the solution ratio of free glycoprotein IIbIIIa receptor to occupied glycoprotein IIbIIIa receptor. In addition, the amount of the complex comprising the second biological molecule, the first component, and the different second component is a measure of the solution ratio of activated platelets to inactive platelets.

In a preferred embodiment the invention relates to the method of determining the ratios of three or more biological molecules, where the second component has specific binding affinity for either free glycoprotein IIbIIIa receptor or occupied glycoprotein IIbIIIa receptor, and the different second component has specific binding affinity for P-selectin.

In another preferred embodiment the invention relates to the method of determining the ratios of three or more biological molecules, where the method further comprises another different second component having specific binding affinity for a third biological molecule. This other different second component can comprise a specific recognition moiety.

In another preferred embodiment the invention relates to the method of determining the ratios of three or more biological molecules, where the first component is specific for glycophorin, where the second component has specific binding affinity for free glycoprotein IIbIIIa receptor, where the different second component has specific binding affinity for P-selectin, and where the other different second component has specific binding affinity for occupied glycoprotein IIbIIIa receptor.

In an aspect that bears on the foregoing embodiments and aspects of the invention, components of the invention can have specific binding affinity to two or more biological molecules, where the biological molecules are (a) related, (b) not related, or (c) related and not related.

Examples of components that have specific binding affinity for biological molecules that are not related are illustrated in FIG. 2. FIG. 2A illustrates a component that comprises a single antibody, where the antibody has specific binding affinity for molecule A and molecule B. Molecule A and molecule B may not be related, and binding of molecule A prevents binding of molecule B. Similarly, binding of molecule B prevents the binding of molecule A to the component.

FIG. 2B illustrate another component that can bind biological molecules that are not related, where the component comprises two antibodies, each having specific binding affinity for one biological molecule, either molecule A or molecule B. The antibodies of the component can be arranged in space such that binding of molecule A to the component prevents the binding of molecule B to the component, and binding of molecule B prevents binding of molecule A.

The term "related biological molecules" as used herein can refer to biological molecules having significant structural similarity to one another. Such related molecules can have substantial amino acid sequence identity between one another or can have substantial nucleic acid sequence identity with one another. Amino acid sequence identity and nucleic acid sequence identity are well known in the art. Examples of related biological molecules are isoforms of a given biological protein, such as hemoglobin and hemoglobin A1-C, oxidized and reduced troponin I, occupied and unoccupied cell surface receptors, or occupied and unoccupied cell receptors.

Biological molecules that are not related may have structural dissimilarities. Such structural dissimilarities may be reflected in amino acid sequence identities and nucleic acid sequence identities that are lower than those for related biological molecules. Examples of biological molecules that are not related are hemoglobin and troponin I, or myoglobin and troponin I. These examples are not meant to be limiting and the invention relates to any biological molecules that are not related.

In FIGS. 1A, 1B, 1C, and 1D, molecules A, B, C, and D may be related, not related, or a mixture thereof. In applications of the invention that concern the determination of one or more ratios of non-related molecules, components illustrated in FIG. 2 can be utilized to bind any non-related biological molecules. Such components illustrated in FIG. 2 can be utilized as components for binding non-related biological molecules in any one of the schemes illustrated in FIGS. 1A, 1B, 1C, and 1D. For example, in methods for determining the ratio of non-related biological molecules, component 1 of FIG. 1A can resemble the component illustrated in FIG. 2, where the component can bind any of the non-related biological molecules, and where binding of one molecule precludes the binding of another non-related molecule.

In another aspect, the invention relates to a kit for determining the ratio of biological molecules. The kit comprises the following elements: (a) a first component having specific binding affinity to the biological molecules, where the biological molecules bind to the first component in an amount that is proportional to their ratio in the sample for the first component; and (b) a second component having specific binding affinity for one or more of the biological molecules. The kit may also comprise a label or Food and Drug Administration approved protocol indicating the steps for determining the ratio.

The term "kit" as used herein refers to a packaged product comprising components of the invention used to determine the ratio of biological molecules. The kit preferably comprises a box or container that holds the components of the kit. The box or container is affixed with a label or a Food and Drug Administration approved protocol. The box or container holds components to the invention which are preferably contained within plastic, polyethylene, polypropylene, ethylene, or propylene vessels. The vessels can be capped tubes or bottles.

The term "label" as used herein can refer to an indicator on the outside of a kit. The label can be constructed from material or another material such as plastic.

Alternatively, the term "label" as used herein can be used to describe a "signal generator" or "signal generating element" or "reporter molecule."

In a preferred embodiment, the invention relates to the kit for determining the ratio of biological molecules, where at least one of the components comprises an antibody. In this preferred embodiment, the first component can comprise an antibody, the second component can comprise an antibody, or the first component and the second component can comprise antibodies. Thus, the method can utilize a first component that comprises an antibody and a second component that comprises another type of polypeptide or organic molecule. Alternatively, the method may relate to two components that comprise antibodies.

In yet another preferred embodiment, the invention relates to the kit for determining the ratio of biological molecules, where at least one of the components comprises a reporter molecule. In this preferred embodiment, the first component can comprise a reporter molecule, the second component can comprise a reporter molecule, or the first component and the second component can comprise reporter molecules. If both components comprise reporter molecules, the reporter molecules may be the same types of molecules, or preferably, different types of reporter molecules.

In another preferred embodiment the invention relates to the kit for determining the ratio of biological molecules, where at least one component comprises a specific recognition moiety. In this preferred embodiment, the first component can comprise a specific recognition moiety, the second component can comprise a specific recognition moiety, or the first component and the second component can comprise specific recognition moieties. If both components comprise specific recognition moieties, the specific recognition moieties may be different from one another or the same recognition moiety.

In another preferred embodiment the invention relates to the kit for determining the ratio of biological molecules, where at least one of the components comprises a linkage to a solid support. In this preferred embodiment, the first component can comprise a linkage to a solid support, the second component can comprise a linkage to a solid support, or both the first and the second component can comprise linkages to solid supports. If both components comprise linkages to solid supports, the solid supports may be different types of solid supports, or are of the same type of solid support, but each type of component is linked to discrete solid support entities. The term "discrete solid support entities" as used herein refers to one component linked to one solid support and another type of component linked to another solid support, where the solid support composition may be the same of different.

In another preferred embodiment, the invention relates to the kit for determining the ratio of biological molecules, where the second component has specific binding affinity for a complex comprising, consisting of, or consisting essentially of one biological molecule and the fist component. The invention is preferably practiced in the manner stated by this preferred embodiment when the concentration of an unbound biological molecule exceeds the concentration of the second component to which that biological molecule specifically binds. The second component can bind a complex of one or more molecules when a binding region of the second component has specific binding affinity to a region on a biological molecule and an adjacent region on the first component. Examples of bifunctional organically synthesized molecules as well as antibodies that bind complexes exist in the art.

In a preferred embodiment, the invention relates to the kit for determining the ratio of biological molecules, where the first component comprises a binding moiety having specific binding affinity for each of the biological molecules of interest. Each of the molecules bind to the first component in a ratio related to their solution ratio. For example, a binding moiety may have specific binding affinity for a modified molecule and its related unmodified form: a binding moiety may have specific binding affinity for hemoglobin and its modified form, hemoglobin A1-C. The binding moiety may bind to the modified and unmodified forms of biological molecules with equal affinity or unequal affinity.

If the two forms of the biological molecules bind to the first component with unequal affinity, a normalization factor can be determined to correct for the actual ratio of the biological molecules bound to the first component. Alternatively, the ratio can be simply determined using a standard curve constructed as described herein by example.

In another preferred embodiment, the invention relates to the kit for determining the ratio of biological molecules, where the first component comprises: (a) a first binding moiety having specific binding affinity for one biological molecule; and (b) a second binding moiety having specific binding affinity for another of the biological molecules of interest. In this preferred embodiment, the first component can bind each of the biological molecules of interest, but is constructed such that each of the biological molecules compete for it. Specifically, the biological molecules may only bind to one of the biological molecules of interest at one time. The invention can also relate to a first component in which the first binding moiety has specific binding affinity for one biological molecule and a second binding moiety has specific binding affinity for one or more other biological molecules. In this manner, a ratio can be determined for one molecule to a family of molecules if desired. Preferably, the ratio is determined for one biological molecule to one other biological molecule.

In other preferred embodiments, the invention relates to the kit for determining the ratio of biological molecules, where one or more of the binding moieties of the first component or second component are antibodies.

In yet another preferred embodiment, the invention relates to the kit for determining the ratio of biological molecules where the first component is specific for both occupied receptor and free receptor, and where the second component is specific for: (a) occupied receptor; (b) free receptor; (c) a complex comprising, consisting essentially of, or consisting of occupied receptor and the first component; or (d) a complex comprising, consisting essentially of, or consisting of free receptor and the first component.

In another preferred embodiment, the invention relates to the kit for determining the ratio of biological molecules, where the first component is specific for both hemoglobin and hemoglobin A1-C, and where the second component is specific for: (a) hemoglobin; (b) hemoglobin A1-C; (c) a complex comprising, consisting essentially of, or consisting of hemoglobin and the first component; or (d) a complex comprising, consisting essentially of, or consisting of hemoglobin A1-C and the first component.

In yet another preferred embodiment the invention relates to the kit for determining the ratio of biological molecules, where the first component is specific for both oxidized troponin I and reduced troponin I and where the second component is specific for: (a) oxidized troponin I; (b) reduced troponin I; (c) a complex comprising, consisting essentially of, or consisting of oxidized troponin I and the first component; or (d) a complex comprising, consisting essentially of, or consisting of reduced troponin I and the first component.

Another preferred embodiment relates to the kit for determining the ratio of biological molecules, further comprising a third component, where the third component has specific binding affinity for a complex comprising the first biological molecule and the second component. The third component may comprise a specific recognition moiety.

In another preferred embodiment the invention relates to the kit for determining the ratio of biological molecules, where the kit further comprises a different second component, and where the different second component has specific binding affinity for a second biological molecule. The different second component can comprise a specific recognition moiety.

In yet another preferred embodiment the invention relates to the kit for determining the ratio of biological molecules, where the kit further comprises another different second component, and where this other different second component has specific binding affinity for a third biological molecule. This other different second component can comprise a specific recognition moiety.

In another preferred embodiment the invention relates to the kit for determining the ratio of biological molecules, where the first component is specific for glycophorin, where the second component has specific binding affinity for either free glycoprotein IIbIIIa receptor or occupied glycoprotein IIbIIIa receptor, and where the third component has specific binding affinity for P-selectin.

Another preferred embodiment relates to the kit for determining the ratio of biological molecules further comprising the biological molecules themselves. The biological molecules are in a purified form suitable for determining the ratio of the biological molecules.

The term "purified form" as used herein refers to the degree of heterogeneity of the biological molecules. Multiple purification processes are known to those skilled in the art. An example of a purification process is high performance liquid chromatography using ion exchange, size exclusion, and hydrophobic techniques. These processes can be applied to proteinaceous molecules as well as organic molecules.

The term "suitable for determining the ratio" as used herein refers to a purified form of the biological molecules that yields reproducible results in the method described on the label of the kit. The term refers to a level of purity such that other molecules do not significantly interfere with the binding between the components of the invention and the biological molecules of the invention.

In yet another preferred embodiment, the invention relates to a kit for determining the ratio of biological molecules where the biological molecules are occupied receptor and free receptor.

In another preferred embodiment, the invention relates to a kit for determining the ratio of biological molecules where the biological molecules are hemoglobin and hemoglobin A1-C.

In a preferred embodiment the invention relates to a kit for determining the ratio of biological molecules where the biological molecules are oxidized troponin I and reduced troponin I.

In another preferred embodiment the invention relates to the kit for determining the ratio of biological molecules where the biological molecules are glycophorin, free glycoprotein IIbIIIa receptor, occupied glycoprotein IIbIIa receptor, and P-selectin.

The summary of the invention described above is not limiting and other features and advantages of the invention will be apparent from the following detailed description of the invention, and from the claims.

The summary of the invention described above is not limiting and other features and advantages of the invention will be apparent from the following detailed description of the invention and from the claims.

Part A depicts an embodiment where a first component of the invention, which is linked to a reporter molecule, binds biological molecules A and B in a fluid sample in a binding ratio related to the solution ratio of A and B. The concentration of the first component in the fluid sample is less than the concentration of the biological molecules. A second component of the invention, which is linked to a solid support, specifically binds to only biological molecule B. The concentration of the second component in the fluid sample is greater than, equal to, or less than the concentration of the first component. Unbound molecules are washed away from the solid support and the complex comprising the first component, the second component, and biological molecule B is detected by virtue of the signal generated from the reporter molecule linked to the first component. The signal relates to the ratio of biological molecules A and B in the fluid sample.

Part B of FIG. 1 depicts another embodiment of the invention where a third component is utilized to determine the ratio of the biological molecules in a fluid sample. The concentration of the third component is greater than the concentration of the second components. Unlike the embodiment described in part A, the second component is not linked to a solid support. The third component, which may be linked to a solid support, has specific binding affinity for the complex comprising the second component and biological molecule B. The ratio is then determined after washing unbound molecules away from the solid support and measuring the signal generated from the complex comprising the first component, the second component, the third component, and biological molecule B.

Part C of FIG. 1 illustrates an embodiment of the invention in which multiple first components and multiple second components are utilized to measure two or more ratios of multiple biological molecules. The concentration of the first components are less than the concentrations of the biological molecules, respectively, to which they respectively bind and the concentrations of the second component are less than, equal to, or greater than the concentrations of the first components.

Part D of FIG. 1 depicts an embodiment of the invention in which one first component is utilized in conjunction with multiple second components of the invention. The concentration of the first component is less than the concentration of the biological molecules and the concentrations of the second components are less than, equal to, or greater than the concentration of the first component.

The embodiments of the first component described by FIG. 1 are found useful in measuring the ratio of biological molelcules, where the biological molecules binding to the first component have the same or similar epitope.

Figure 1A:
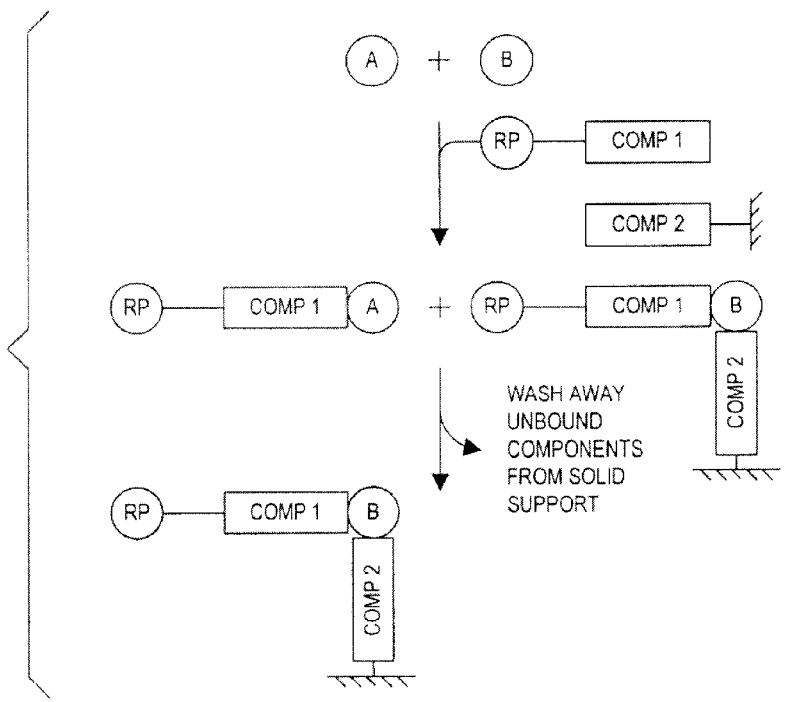
FIG. 1 illustrates two embodiments of the invention.
Figure 1B:
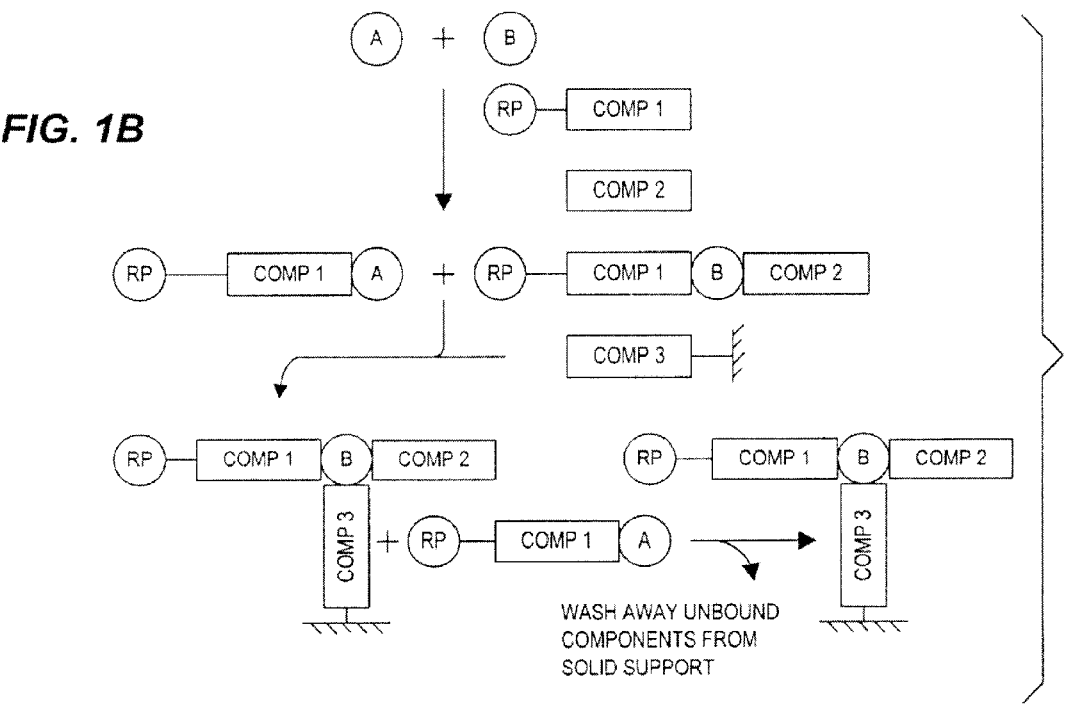
Figure 1C:
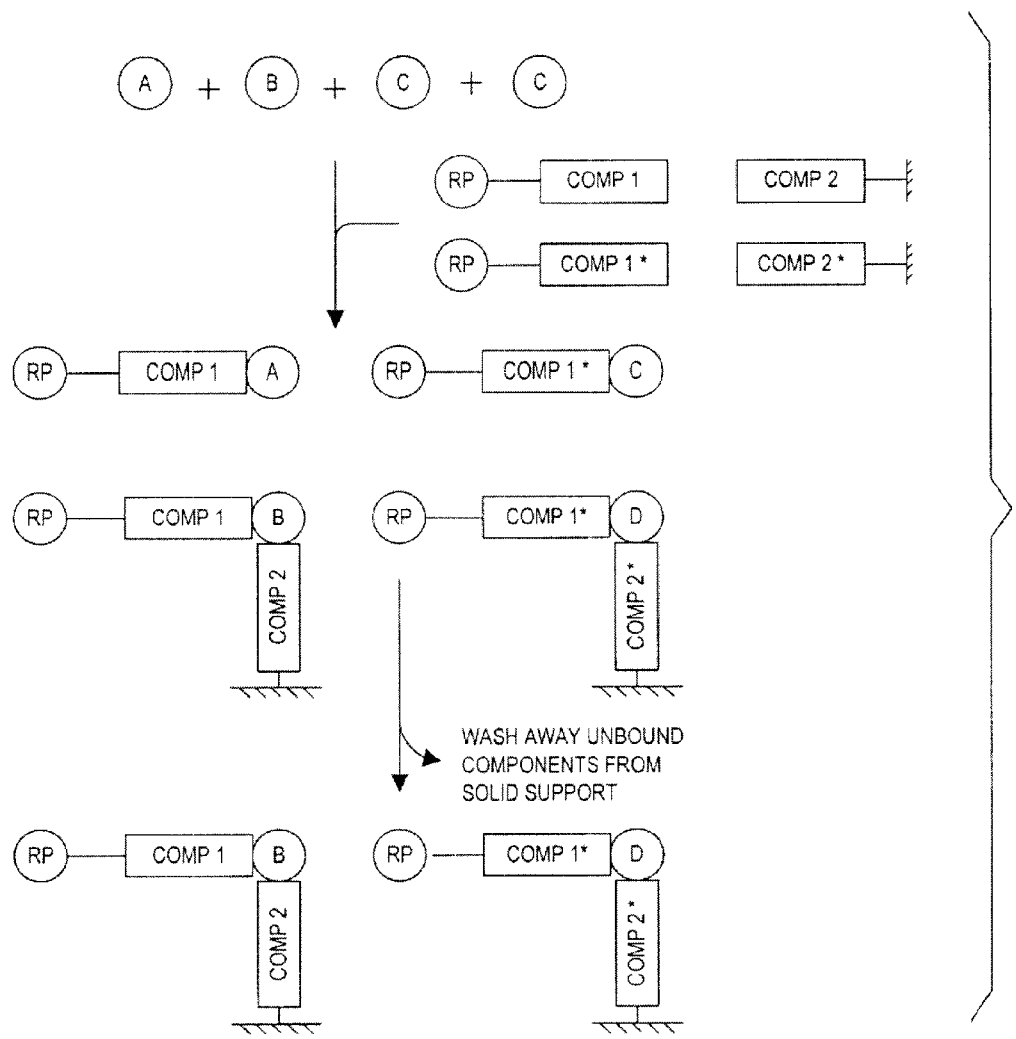
Figure 1D:
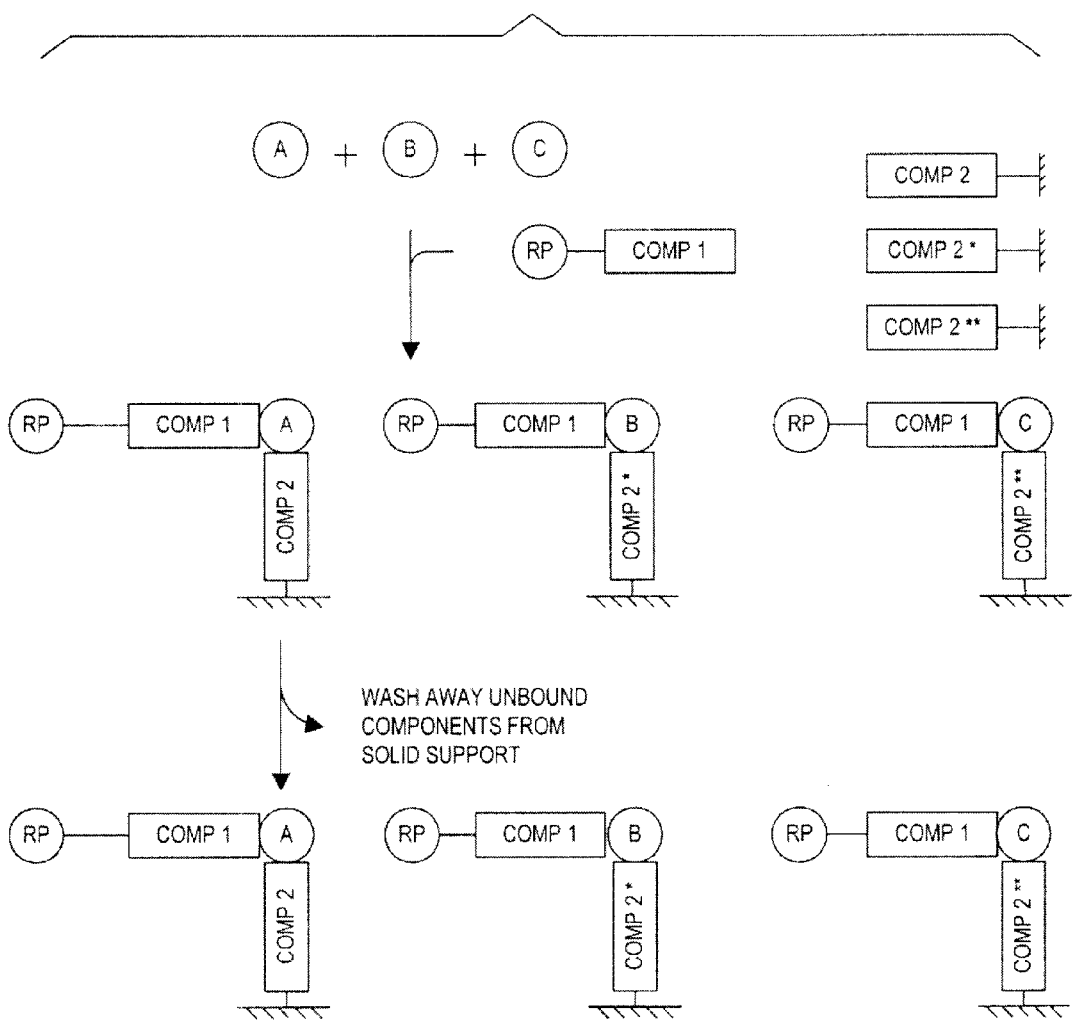
Figure 2A:
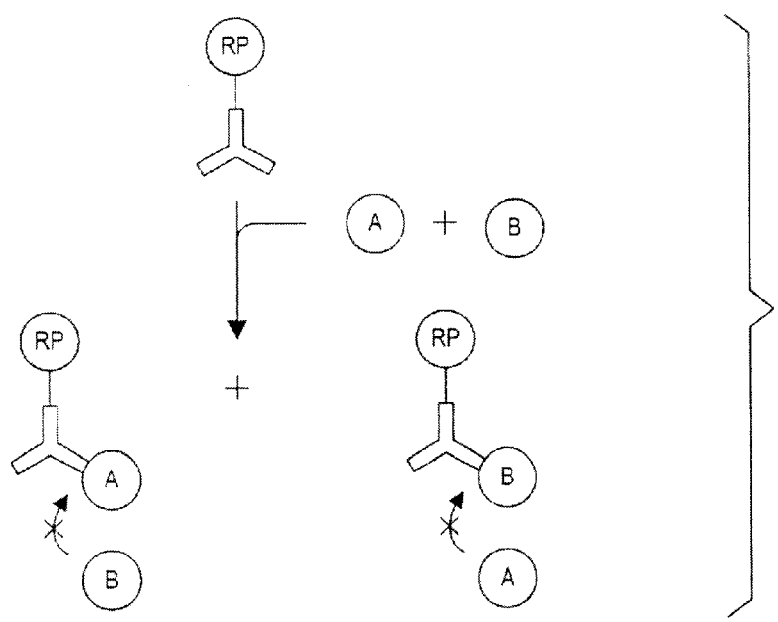
Figure 2B:
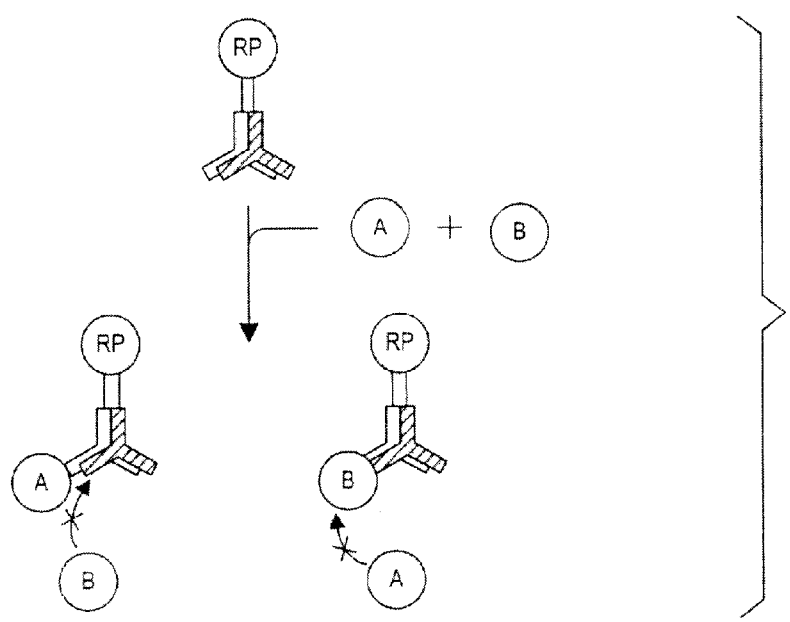

FIG. 2 depicts two embodiments of the invention directed towards the first component.

Part A describes a first component that comprises an antibody linked to a reporter molecule. The first component can comprise multiple reporter molecules or multiple antibodies. The concentration of the first component in the fluid sample is less than the concentration of the biological molecules. The binding moieties of the antibody in this embodiment can independently bind specifically to each of the biological molecules A and B, but the binding of either A or B excludes the binding of the other. For example, once one A molecule binds to a binding moiety of the antibody, a molecule of B cannot occupy that position at the same time.

Part B describes a first component that comprises two distinct antibodies linked to a reporter molecule. The first component can comprise multiple reporter molecules or multiple molecules of each type of antibody. The concentration of the first component in the fluid sample is less than the concentration of the biological molecules. One of the distinct antibodies specifically binds biological molecule A and one of the distinct antibodies specifically binds biological molecule B. The distinct antibodies are arranged such that the binding of either A or B excludes the binding of the other. For example, once one A molecule binds to a binding moiety on one of the distinct antibodies, a molecule of B cannot bind to an adjacent binding moiety at the same time.

The embodiments of the first component described by FIG. 2 are found useful in measuring the ratio of biological molecules, where the biological molelcules binding to the component have distinct epitopes, for example. In addition, the biological molecules binding to the component can have different epitopes on the same or similar biological molecules or different epitopes on different biological molecules.

DETAILED DESCRIPTION OF THE INVENTION

The invention relates in part to a novel method of rapidly determining the ratio of biological molecules without quantifying the concentrations of each biological molecule of the ratio. The invention also relates in part to a kit for determining the ratio of biological molecules.

Existing methods for determining ratios of biological molecules involve multiple steps and cannot be applied to a number of systems. These existing methods involve multiple steps since they utilize at least one component, usually an antibody, specific for each one of the biological molecules. Thus, at least two assays are required to determine the ratio of biological molecules in most cases. Hence, most of these existing systems prolong the time required to determine the ratio, and, in addition, accumulate reagent costs.

Furthermore, the existing methods for determining the ratios of biological molecules utilize at least one component, usually an antibody, that is in excess of the biological molecules in the sample. Because some relevant biological molecules, such as hemoglobin and cell receptors, exist at high concentrations in biological fluids, existing methods that utilize components in excess of the biological molecules are of limited application.

The present invention increases the rate at which ratios of related biological molecules are determined by utilizing a component that binds to each of the biological molecules and another component that specifically binds to only one of the biological molecules. These two components can be added together to the sample containing the biological molecules in the same reaction vessel at the same time. This feature enhances the rate at which the ratio is determined by reducing the number of steps involved in the process.

The rapid rate of determining the ratio of biological molecules can enhance the recovery of patients suffering from medical conditions. Proper treatment of these conditions can therefore be expedited since diagnosis results can be produced rapidly by the methods disclosed herein. In particular, applications of the methods and kits described herein relate in part to increasing the efficiency of monitoring drug delivery, monitoring the blood-glucose level in diabetic patients, and monitoring the time of myocardial infarction.

In the case of heart attacks, for example, a rapid determination of the oxidized to reduced troponin I ratio will hasten the determination of the time of a myocardial infarction, and thereby expedite the administration of a proper treatment to the patient. Expediting the treatment of a patient will improve that patient's recovery from the myocardial infarction.

The rapid rate of determining the ratio of related biological molecules can also enhance the delivery of a therapeutic drug to a patient. In the case of a drug that binds and blocks a cell surface receptor, a rapid determination of the free receptor to occupied receptor ratio can determine whether a larger or smaller dose of the drug should be delivered to the patient for an effective therapy.

Furthermore, the invention allows for the determination of ratios of related biological molecules that exist at high concentrations in a sample. Hemoglobin, for example, exists at high concentrations in a patient's blood stream. Hemoglobin becomes hemoglobin A1-C when it is modified with glucose moieties in the presence of high glucose concentrations in the patient's blood stream. One component of the invention can isolate a fraction of the total hemoglobin molecules that comprises the ratio of hemoglobin and hemoglobin A1-C in the sample (hemoglobin and hemoglobin A1-C) and a second component can isolate one of the related molecules (such as hemoglobin A1-C) to determine the ratio of these related molecules even when they exist at high concentrations in a sample. This application of the methods described herein is useful for diabetic patients since hemoglobin A1-C represents the average blood glucose concentration over periods of time longer than one day. Because diabetic patients often cannot accurately determine their blood glucose levels due to variable readings using the techniques currently available to them, the methods and kits of the invention provide for the accurate and rapid determination of the average blood glucose level for diabetic patients.

I. Components of the Invention

A person of ordinary skill in the art can rapidly determine the ratio of biological molecules by utilizing the methods of the invention. The methods of the invention include one type of binding molecules, preferably antibodies, that recognize each of the biological molecules in a sample, and another type of components that bind only one of the biological molecules.

FIG. 1, which depicts one embodiment of the invention, serves as an illustrative example for the rapid determination of the ratio of biological molecules. The number of steps are reduced by probing a sample with a first component that binds a fraction of each of the biological molecules of interest. The concentration of the first component is less than the concentration of the biological molecules. In addition to binding a fraction of each of the biological molecules, the binding of one of the biological molecules to the first component excludes the binding of the other, even though the first component has the capacity of binding each of the molecules independently.

These two features of the first component, the multiple binding feature and the exclusive binding feature, allow the first component to bind the biological molecules in a ratio that is proportional to their ratio in the sample. For example, if the first component can bind each of molecules A and B, and A and B exist in the sample at a 3 to 1 ratio, the first component can also bind A and B in a 3 to 1 ratio, or nearly this ratio. Biological molecules A and B bind to the first component in a similar ratio as they exist in solution when the first component binds A and B with high affinity (when the equilibrium dissociation constant is less than the concentrations of A and B and the first component) and/or when A and B bind the first component with equal affinity. Thus, the ratio of A to B can be bound to the first component in a ratio similar to the ratio of A to B existing in a sample probed with the first component.

The second component of the invention which can be greater than equal to, or less than the concentration of the first component, detects the complex formed between the first component and one of the biological molecules. This complex may be detected when the second component binds to only one of the biological molecules, e.g., A or B, or if the second component binds to the complex formed between one of the biological molecules and the first component. The latter instance may provide an advantage if the biological molecules exist at high concentrations in the sample with respect to the concentration of the second component, since the second component will bind the complex comprising one biological molecule and the first component and not the unbound biological molecule.

Once the second component binds the complex comprising the first component and a biological molecule, a signal can be measured from a reporter molecule linked to one of the components of the invention. This signal can be applied to a standard curve that relates the signal to a ratio of the biological molecules. The standard curve can be prepared by measuring the signal, by the methods, described herein, for samples prepared with known ratios of the biological molecules.

When biological molecules do not bind to the first component with equal affinity, standard curves relating the ratio to a signal generated by one of the components, preferably the first component, can be utilized to determine the ratio of A to B in the sample. In addition, normalization factors can be utilized to determine the ratio of A to B in a sample.

Furthermore, the components of the invention determine the ratio of biological molecules when they exist at concentrations exceeding the concentrations of the first component in a sample. Thus, the ratio of biological molecules can be determined rapidly in essentially one step. This feature represents an improvement over many existing methods, for example, sandwich or noncompetitive immunoassays, for determining the ratio of biological molecules as the existing methods require that the concentrations of the first and second components exceed the concentrations of the biological molecules. Using existing methods, for example, competitive and non-competitive immunoassays, the ratio of the biological molecules is determined after measuring the concentrations of both biological molecules. This invention measures the ratio directly, circumventing the need for measuring the individual concentrations of the biological molecules that comprise the ratio or ratios. One skilled in the art will recognize that the relative concentrations of more than two biological molecules can be determined by the methods of the invention.

The components of the invention can be constructed using techniques well known to those skilled in the art. Reporter molecules can be linked to one or more proteins or antibodies using standard techniques reported in Harlo and Lane, *Antibodies, a Laboratory Manual,* 1989, Cold Spring Harbor Laboratories. This manual also reports techniques for linking antibodies and other protein molecules to solid supports. Alternatively, chemical synthetic techniques are well known to those skilled in the art which can be employed to attach reporter molecules and/or solid supports to components of the invention.

II. Biological Molecules of the Invention

The methods of the invention can relate to a variety of biological molecules. The methods of the invention are especially adapted to measuring the ratio of proteins or peptides in a biological sample. Those proteins or polypeptides include hormones, growth factors, enzymes, clotting factors, structural proteins, muscular proteins, blood proteins, receptor proteins, apolipoproteins, receptors, drugs, oncogenes, tumor antigens, tumor suppressors, cytokines, viral antigens, parasitic antigens, bacterial antigens and chemically synthesized polymers and polymers biosynthesized and/or modified by chemical, cellular and/or enzymatic processes. Specific examples of these compounds include oxidized troponin I, reduced troponin I, glycophorin, glycoprotein IIbIIIa receptor, hemoglobin, hemoglobin A1-C, proinsulin, insulin, growth hormone, androgen receptors, insulin-like growth factor I, insulin-like growth factor II, insulin growth factor binding proteins, epidermal growth factor, TGF-$\alpha$, TGF-$\beta$, dermal growth factor (PDGF), angiogenesis factors (acidic fibroblast growth factor, basic fibroblast growth factor and angiogenin), matrix proteins (Type IV collagen, Type VII collagen, laminin), oncogenes (ras, fos, myc, erb, src, sis, jun), E6 or E7 transforming sequence, p53 protein, cytokine receptor, IL-1, IL-6, IL-8, IL-2, $\alpha$, $\beta$, or $\gamma$IFN, GMCSF, GCSF, viral capsid protein, and proteins from viral, bacterial and parasitic organisms. Other specific proteins or polypeptides which can be expressed include: phenylalanine hydroxylase, $\alpha$-1-antitrypsin, cholesterol-7$\alpha$-hydroxylase, truncated apolipoprotein B, lipoprotein lipase, apolipoprotein E, apolipoprotein A1, LDL receptor, scavenger receptor for oxidized lipoproteins, molecular variants of each, VEGF, and combinations thereof. Other examples are clotting factors, apolipoproteins, drugs, tumor antigens, viral antigens, parasitic antigens, and bacterial antigens. One skilled in the art readily appreciates that these proteins belong to a wide variety of classes of proteins, and that other proteins within these classes and drugs and organic compounds can also be used. These are only examples and are not meant to be limiting in any way.

III. Method for Determining the Time of a Myocardial Infarction Using Components of the Invention Myocardial infarction is one of the leading causes of death in the United States. Approximately five million individuals experiencing chest pain are evaluated every year in hospitals throughout the United States. However, less than thirty percent of these individuals are subsequently found to have had a myocardial infarction. The accurate and rapid diagnosis of myocardial infarction is important for the patient suffering a myocardial infarction and for the health care system. the health care system can minimize costs incurred through treating patients who never suffered a myocardial infarction by rapidly identifying individuals who do need treatment. In addition, rapidly determining the time of myocardial infarction in patients who indeed suffered a heart attack can expedite this treatment and thereby enhance that recovery process.

The diagnosis of myocardial infarction is currently performed in the emergency department of a hospital. An individual having the symptoms of myocardial infarction is treated in different ways depending on the obviousness of the condition. Generally an electrocardiogram is given to assess the condition of the heart; however, approximately fifty percent of patients experiencing myocardial infarction experience a non-diagnostic electrocardiogram. The physician is then faced with a problem of diagnosing and treating the patient suspected of having a myocardial infarction. Thus, diagnosis is difficult for patients with a suspected myocardial infarction who have non-diagnostic electrocardiograms.

The World Health Organization has instituted guidelines for diagnosing myocardial infarction. These guidelines state that an individual must exhibit two of the three following criteria: (1) have chest pain or a history of cardiac disease; (2) a diagnostic electrocardiogram; and (3) elevated creatine kinase or creatine kinase MB isoenzyme. Thus, for the fifty percent of the individuals who are presented to hospitals for a suspected myocardial infarction and who have a non-diagnostic electrocardiogram, the physician must rely on symptoms of chest pain and elevated creatine kinase levels to diagnose a myocardial infarction.

The assay of creatine kinase is generally performed in hospital laboratories using sophisticated, expensive, and elaborate instrumentation. The assays include enzyme assays and immunoassays which detect the activity or mass of creatine kinase present in blood samples. Thus, a simpler and more rapid technique is required for more efficient and more accurate assessments of myocardial infarction.

The measurement of the ratio of oxidized to reduced troponin I represents such an efficient and accurate technique for assessing the time of myocardial infarction. During a myocardial infarction heart muscle cells die and release their contents to the bloodstream. Troponin I is one such muscle content that is released into the blood after a myocardial infarction. In addition, creatinine kinase is released into the bloodstream after a myocardial infarction. The concentrations of troponin I as well as creatine kinase become elevated above an otherwise nominal value in the blood after a myocardial infarction. The presence of these molecules in the bloodstream can be diagnostic of a myocardial infarction. Troponin I has recently been shown to be more specific than creatine kinase for diagnosing myocardial infarction. (*Circulation* 83, 902–912, 1991); *Clin. Chem.* 40, 1291–1295 (1994). The use of troponin I as a diagnostic marker for myocardial infarction also appears to meet many of the clinical requirements. *Clin. Chem.* 40, 1291–1295–1994–; *Clin. Chem.* 41, 312–317 (1995).

A method of determining the time of a myocardial infarction takes advantage of the ratio of oxidized to reduced troponin I in a sample taken from a patient. Preferably, a patient's fluids, particularly blood, serum, and plasma, are extracted from the patient's body before analysis of the ratio. The degree to which troponin I is oxidized in the blood sample is diagnostic for the time of the myocardial infarction. PCT publication WO 96/33415 incorporated by reference herein in its entirety, including all figures, tables, and drawings, indicates that troponin I can exist in various conformations in the blood which may be the same or different than its native conformation and muscle tissue. The various conformations of the troponin I can react in different manners with components of the invention.

The components of the present invention provide a rapid determination for the ratio of oxidized to reduced troponin I. A blood sample can be probed simultaneously with the first and second components of the invention. The first component can specifically bind to both oxidized and reduced troponin I, in a ratio dependent manner. The second component of the invention can specifically bind oxidized troponin I or reduced troponin I, or complexes formed between one of the forms of troponin I and the first component. The second component forms a complex comprising one of the forms of troponin I, the first component, and the second component determines the ratio of oxidized troponin I to reduced troponin I as measured from a standard curve previously generated from known ratios of oxidized and reduced troponin I. The standard curve can relate any signal generated by a reporter molecule linked to one of the components of the invention to the ratio of oxidized to reduced troponin I.

IV. Method for Enhancing the Therapeutic Effect of a Drug Delivered to a Patient Using components of the Invention The rapid determination of the ratio of biological molecules, as featured herein, can enhance the effective delivery of a therapeutic drug. In the case of a drug that binds a cell surface receptor, a rapid determination of the free receptor to occupied receptor ratio can determine whether a larger or smaller dose of the drug should be delivered to the patient for an effective therapy. The drug can be a naturally occurring ligand, or alternatively, a synthetic molecule that binds the receptor with high affinity. In such an application, after a patient is delivered a drug a fluid sample is assayed for the ratio of free receptor to occupied receptor using the methods of the invention.

An example of a pharmaceutically relevant free/occupied receptor system relates to receptor glycoprotein IIbIIIa and its role in thrombosis. Thrombosis is the process in which red blood cells form a clot upon binding fibrinogen. Various drugs already in the market or entering the market can bind to the glycoprotein IIbIIIa receptor and block the clotting process.

The methods set forth herein measure two events associated with aggregation. The first is the degree of occupancy of the receptor glycoprotein IIbIIIa. The second is the degree of activation of the platelets. The relative degrees of receptor occupancy on platelets and platelet activation can be determined simultaneously as described in Example 2. These parameters are important for understanding the events leading to a thrombosis and also to the dosing of drugs that prevent thrombosis by binding to the glycoprotein IIbIIIa. A method for measuring the concentration of drug that should be administered to a patient by monitoring these events is provided herein by example.

The first component of the invention, specific for occupied and free receptor or an epitope of the component defining the occupied and free receptor, and the second component of the invention, specific for either the free receptor or the occupied receptor, can be added to a sample prepared from the patient. The signal generated from the sample determines the ratio of occupied to free receptor as extrapolated from a standard curve prepared in advance.

A high free receptor to occupied receptor ratio would suggest that a larger dose of the drug needs to be delivered to the patient in the next administration. Alternatively, a low free receptor to occupied receptor ratio would specify that the same or lower concentration of drug should be administered to the patient for the next administration.

There remains a great need in the art for a method of rapidly determining a ratio of free receptor to occupied receptor. An increasing number of drugs that bind receptors with high affinity are currently entering the market. Effective administration of these types of drugs require a rapid determination of the ratio of free receptor to occupied receptor, as provided herein.

V. Method for Managing Diabetes Using Components of the Invention

Diabetes mellitus is a heterogenous primary disorder of carbohydrate metabolism with multiple etiologic factors that generally involve insulin deficiency or insulin resistance or both. Type I, or Juvenile Onset, or Insulin-Dependent Diabetes Mellitus is present in patients with little or no endogenous insulin secretory capacity. These patients develop extreme hyperglycemia and are entirely dependent on exogenous insulin therapy for immediate survival. Type II, or Adult-Onset, or Non-Insulin-Dependent Diabetes Mellitus occurs in patients who retain some endogenous insulin secretory capacity, however the great majority of them are both insulin deficient and insulin resistant. Insulin resistance can be due to insufficient insulin receptor expression, reduced insulin-binding affinity, or any abnormality at any step along the insulin signaling pathway. Olefsky, 1988, *Cecil Textbook of Medicine,* 18th Edition, 2:1360–1381.

Overall, in the United States the prevalence of diabetes is probably between two and four percent, with Type I comprising seven to ten percent of all cases. Secondary complications of diabetes have serious clinical implications. Approximately twenty-five percent of all new cases of end-stage renal failure occur in patients with diabetes. About twenty thousand amputations (primarily of toes, feet, and legs) are carried out in patients with diabetes, representing approximately half of the non-traumatic amputations performed in the United States. Furthermore, diabetes is the leading cause of new cases of blindness, with approximately five thousand cases occurring each year.

Insulin is the primary mode of therapy in all patients with Type I and in many with Type II diabetes. Depending on the number of injections per day and type(s) of insulin used, the regimen can be more or less intensive. The most intensive consists of constant insulin delivery into a subcutaneous site in the abdominal wall via an open loop delivery device consisting of a small insulin pump that must be worn by the patient essentially twenty-four hours per day. Oral hypoglycemic agents such as sulfonyl ureas are effective in Type II patients but approximately ten to twenty percent of patients do not respond or cease to respond twelve to twenty-four months after beginning treatment.

Effective control of glucose levels is difficult to achieve for prolonged periods even with the most meticulous mode of insulin therapy in the most motivated patients. Transplantation of the pancreas or islet cells, which normally produce insulin, continues to receive extensive study as a potential treatment. In addition, efforts towards developing newer and better external or implantable insulin delivery devices integrated with a glucose sensor continues. However, because these methods have not come to fruition, there remains a need in the medical profession for a method that accurately assesses the average level of glucose in a patient's bloodstream over time.

The method of determining the ratio of hemoglobin A1-C and hemoglobin represents a method for the rapid determination of the average concentration of glucose in a patient's bloodstream. Hemoglobin exists at high concentrations in a patient's bloodstream. Hemoglobin becomes hemoglobin A1-C when it is modified with glucose moieties with glucose in the patient's bloodstream. The red blood cells of all persons contain a small proportion of hemoglobin A1-C. The rate of its formation is proportional to the sugar level, and so diabetics have a higher proportion of hemoglobin A1-C than do normal individuals. (Six to fifteen percent compared to three to five percent). The level of hemoglobin A1-C reveals the integral of the blood sugar concentration over a period of several weeks. Hence, measurements of hemoglobin A1-C as a percent of total hemoglobin every several weeks are very useful in determining whether the blood glucose levels of diabetic patients were adequately controlled. Thus, the methods of measuring the ratio of hemoglobin A1-C to hemoglobin as described herein represent a rapid and accurate method of regulating the glucose concentration in the blood of diabetic patients.

The ratio of hemoglobin A1-C to hemoglobin can be measured rapidly using the methods and kits of the invention. The first component, which specifically binds hemoglobin and hemoglobin A1-C, and the second component, which specifically binds to one of these forms of hemoglobin or a complex formed between one of these forms of hemoglobin and the first component, are added together to a blood sample of a patient in one step. The signal delivered from a complex comprising one of the forms of hemoglobin, the first component, and the second component directly determines the hemoglobin A1-C to hemoglobin ratio from a standard curve.

VI. Method of Determining the Ratio of Biological Molecules

The method of the invention, which determines the ratio of biological molecules, comprises the steps of contacting the biological molecules with a first component having specific binding affinity to both biological molecules, while at the same time, contacting the biological molecules with a second component having specific binding affinity for one of the biological molecules as a measure of the ratio. The components of the invention can comprise peptide-based molecules, organic molecules, or preferably antibodies. The biological molecules can comprise but are not limited to organic molecules, peptides, nucleic acids, antibodies, receptors, cells, cell surfaces, and proteins.

Either the first component or second component or both components can be connected to a solid support matrix. This solid support can be composed of a number of materials including agarose, cellulose, polystyrene or a plastic matrix. Preferably, the second component is linked to a solid support by a direct linkage or by a linker between the second component and the solid support.

Either of the two components or both components can also comprise a reporter molecule. The reporter molecule can be a signal generating element comprised of a number of elements: enzymes and their resultant effects on a substrate, colloidal metal particles, latex and silica particles with dye incorporated, and dye particles. An enzyme can catalyze the turnover of a substrate to produce a product that is detectable, for example, by a shift in wavelength detected by absorbance or fluorescence techniques (e.g., ultra-violet, visible, infrared). The enzyme catalyzed product can also be detectable by a shift in the pH of a medium. The signals generated from the reporter molecule can directly reflect the ratio of the biological molecules assayed by the method of the invention, or be used to directly calculate the concentration of the biological molecules.

The first components of the invention can bind to the biological molecules with equal affinity or unequal affinity. If the components of the invention bind to the biological molecules with unequal affinity, a normalization factor can be calculated from experiments that determine the fraction of the components that bind to purified forms of the biological molecules. The normalization factor can be utilized in the method of the invention to minimize the number of steps required for the determination of the ratio of biological molecules.

If antibodies are used as components in the invention, many techniques are well-known to those skilled in the art for the production of antibodies and the modification of antibodies with reporter molecules. These techniques are set forth in WO 96/33415, incorporated herein by reference in its entirety including all figures, drawings and tables. Detailed descriptions of the methods utilized to detect the signal of a reporter molecule, link a reporter molecule to an antibody, link an antibody to a solid support, and other general methods of generating specific antibodies are disclosed in Harlo & Lane, *Antibodies, a Laboratory Manual*, 1989, Cold Spring Harbor Laboratories, incorporated by reference herein in its entirety including any figures or drawings.

The method of the invention can be carried out using a variety of biological samples. Samples can be extracted from a patient, stored in an appropriate solution such that the components do not degrade, and assayed at a later time. Alternatively, the samples can be monitored continuously using a continuous flow apparatus that circulates the patient's bodily fluids through an instrument dedicated to determining the ratio of biological molecules. This continuous flow application would provide a feedback control mechanism particularly useful for the administration of therapeutic compounds to a patient. This application is described herein in reference to determining the ratio of free receptor to occupied receptor. In addition, the methods of the invention can utilize samples prepared from the tissues of a patient. A small amount of tissue can be extracted from a patient, homogenized in an appropriate solution such as a saline solution, filtered, and then assayed using the methods of the invention. Methods of preparing fluid samples as well as tissue samples are well-known to those skilled in the art.

The methods of determining the ratio of biological molecules can be carried out in standard enzyme-linked immunoabsorbent assay formats (ELISA) using microtiter plates. Alternatively, the methods of the invention may be carried out by utilizing a portable instrument designed specifically for this type of method incorporating techniques of homogeneous immunoassays, for example, as described in WO 95/06877, and U.S. Pat. Nos. 3,817,837, 3,935,074, and in *Clin. Chem.* 32, 1637–1641 (1986).

After the related biological molecules have been contacted with the two components of the invention, the complex comprising one biological molecule, the first component and the second component can be detected using standard techniques known to those skilled in the art. These techniques typically involve removing the solution comprising the components of the invention and the biological molecules in the sample which are not part of the complex comprising the biological molecule, the first component, and the second component, and subsequently washing the reaction well in multiple steps or by continuous flow with a solution that does not contain components of the invention or the biological molecules being assayed. The signal that determines the ratio of the biological molecules may be determined without a washing step if the reporter molecules linked to the components of the invention, or the components themselves, change their florescence depolarization, emission wavelength, infrared wavelength, or change any other property after forming the biological molecule/first component/second component complex.

After the washing step, if necessary, the ratio of the biological molecules is typically determined by measuring the signal produced by a reporter molecule. The reporter molecule can be linked to the components themselves or linked to a molecule, such as an antibody, that detects the complex comprising a biological molecule, a first component, and a second component. Preferably, the reporter molecule is linked to the first component of the invention.

The ratio of the related biological molecules can be determined from a signal produced by a reporter molecule linked to one or both of the components of the invention. The signals generated from the method of the invention can be translated into the ratio of the biological molecules by extrapolating the ratio from a standard curve.

A standard curve can be generated by using known amounts of each component being assayed. For example, a signal can be measured from a complex comprising a biological molecule, a first component, and a second component using known concentrations of the biological molecules for which the ratio is determined. The samples containing known amounts of biological molecules can be isolated by purchasing the molecules from commercial sources or by purifying the biological molecules using techniques well known to those skilled in the art. The standard curve can be generated from purified biological molecules prepared in (a) simple in vitro buffered solutions, (b) in vitro solutions mimicking blood conditions, or (c) in vivo samples with known ratios of particular biological molecules, as determined by the concentrations of each of the biological molecules comprising the ratio. The concentrations of each of the biological molecules can be determined from techniques existing in the art. The ratio of biological molecules from the sample of a patient is then extrapolated from a standard curve by applying the signal measured from the sample.

VII. Antibody-Based Method and Kit for Determining the Ratio of Related Biological Molecules The present invention encompasses a method of determining the ratio of related biological molecules in a sample. The method can comprise incubating a test sample with one or more of the antibodies of the present invention and assaying whether the antibody binds to the analytes. Altered levels of the ratio as measured in samples of a patient compared to the ratio determined in normal patients may indicate that an abnormal condition exists in that patient. For example, elevated hemoglobin A1-C to hemoglobin ratios in a patient indicates that patient may be diabetic and/or that patient needs to monitor blood glucose levels more effectively.

Conditions for incubating an antibody with a test sample may vary as appreciated by one of ordinary skill in the art. For example, incubation conditions depend on the format employed in the assay, the detection methods employed, and the type and nature of the antibody used in the assay. One skilled in the art will recognize that any one of the commonly available immunological assay formats (such as radio immunoassays, enzyme-linked immunosorbent assays, diffusion based ouchtelony homogeneous immunoassays, or rocket immuno-fluorescent assays) can readily be adapted to employ the antibodies of the present invention. Examples of such assays can be found, e.g., in Chard "An Introduction to Radio Immunoassay and Related Techniques", Elsevier Science Publishers, Amsterdam, The Netherlands (1986); Bullock et al., "Techniques in Immuno Chemistry", Academic Press, Orlando, Fla. Vol. I (1982), Volume II (1983), Volume III (1985); Tijssen, "Practice and Theory of Enzyme Immunoassays: Laboratory Techniques in Biochemistry and Molecular Biology", Elsevier Science Publishers, Amsterdam, The Netherlands (1985).

A kit in accordance with the invention contains all the necessary reagents to carry out methods of the invention. For example, the kit can comprise: (1) a first container harboring an antibody described herein, (2) a second container harboring a conjugate comprising a binding partner of the antibody, and (3) a label and/or a Food and Drug Administration protocol attached to the outside of the kit container. In another preferred embodiment, the kit further comprises one or more other containers comprising one or more of the following: wash reagents and reagents/materials capable of detecting the presence of bound components or antibodies of the invention.

Examples of detection reagents/materials include, but are not limited to, labeled secondary antibodies capable of specifically binding to antibodies of the invention, or in the alternative, if the primary antibody is labeled, the chromophore, enzymatic, antibody-binding reagents which are capable of reacting with labeled antibody or detection modalities capable of determining the extent of radio activity. One skilled in the art will readily recognize that the antibodies described in the present invention can readily be incorporated into one of the established kit formats which are well-known in the art.

The kit may also include purified forms of each of the biological molecules being assayed in the kit. These purified standard molecules can be utilized by those skilled in the art using the kit to generate a standard curve. The standard curve can be created with the purified molecules in conjunction with the two or three components of the invention.

A standard curve can be generated using the two or three components of the invention in conjunction with the purified biological molecules. Known ratios of the biological molecules can be separately prepared and probed with the two or three components of the invention. A signal generated from the reporter molecule linked to one of the components in the complex comprising the first biological molecule, the first component, the second component, and optionally the third component of the invention can be generated for each ratio of the biological molecules tested. Each signal may be plotted against the ratios in a graph and a curve can be mathematically fit through the data points. This standard curve can therefore relate any measured signal in a biological sample to the ratio of the desired biological molecules in that sample. Other methods associated with the invention are described in examples disclosed herein.

EXAMPLES

The examples below are not limiting and are merely representative of various aspects and features of the present invention. The examples demonstrate methods of determining the ratios of biological molecules. In addition, the examples provide methods of generating a standard curve utilized for the method of the invention, as well as methods of generating normalization factors which can also be utilized by those skilled in the art to carry out the methods of the invention.

Example 1

Method for Determining the Ratio of Free Receptor to Occupied Receptor

The following procedures can be followed by those skilled in the art to determine the ratio of free receptor to occupied receptor in a sample. The ratio of free receptor to occupied receptor can be determined using two different methods. Method A utilizes two components and Method B utilizes three components. Method B provides advantages when the concentration of the biological molecule that specifically binds the second component is greater than the concentration of the second component in a sample.

Method A

1. Prepare an aqueous biological sample. The sample can be a fluid sample extracted from the patient, a fluid sample circulating from the patient to a machine and back to the patient, or a tissue sample.
2. Contact the biological sample with the first and second components of the invention. The first component has specific binding affinity for both free receptor and occupied receptor and its concentration is less that the total concentration of the biological molecules in the fluid sample. The second component is specific for only free receptor or occupied receptor and its concentration in the fluid sample can be greater than, equal to, or less than the concentration of the first component. If the first or second components are not attached to a solid support matrix, one of the components can be attached to a solid support at this step.
3. Wash the solid support with a suitable buffer, such as phosphate buffered saline.
4. Measure a signal from the signal generating (reporter) molecule preferably linked to the first component of the invention.
5. Extrapolate the ratio of free receptor to occupied receptor from the standard curve.

Method B
1. Prepare an aqueous biological sample. The sample can be a fluid sample extracted from the patient, a fluid sample circulating from the patient to a machine and back to the patient, or a tissue sample.
2. Contact the biological sample with the first, second, and third components of the invention. The first component has specific binding affinity for both free receptor and occupied receptor and its concentration is less that the total concentration of the receptor molecules in the fluid sample. The second component is specific for only free receptor or occupied receptor and its concentration in the fluid sample can be greater than, equal to, or less than the concentration of the first component. The third component has specific binding affinity for the complex comprising the second component and either free receptor or occupied receptor. The third component can be directly attached to a solid support or it can be free in solution and comprise a specific recognition molecule, such as a biotin or hemagglutinin tag, that binds to an avidin or anti-hemagglutinin antibody, respectively, attached to a solid support. The concentration of the third component is greater than the concentration of the second component.
3. Wash the solid support with a suitable buffer, such as phosphate buffered saline.
4. Measure a signal from the signal generating (reporter) molecule preferably linked to the first component of the invention.
5. Extrapolate the ratio of free receptor to occupied receptor from the standard curve.

Example 2

Method for Determining the Percent of Glycoprotein Receptor IIBIIIA Bound by Drug and the Percent of Platelets that are Activated The following method can be utilized by a person of ordinary skill in the art to determine the ratio of free glycoprotein IIbIIIa receptor to occupied glycoprotein IIbIIIa receptor and the ratio of activated platelets to inactive platelets. The steps of the process are as follows:
1. Add a first, second, and different second component to a blood sample. The first component is a label-antibody conjugate. The concentration of the first component is less than the concentration of platelets so that all platelet species (e.g. platelets with glycoprotein IIbIIIa receptor that is occupied with a drug, platelets with unoccupied glycoprotein IIbIIIa receptor (inactive platelets), and activated platelets) are bound to the first component in a statistical distribution which is directly proportional to their ratio in the sample. The antibody used for the first component can be selected to specifically bind glycophorin or another molecule on the platelet that is invariant between the four species. The second component is an anti-glycoprotein IIbIIIa antibody/tag1 conjugate. The second component is specific for either the unoccupied glycoprotein IIbIIIa receptor or glycoprotein IIbIIIa receptor occupied with a drug. The different second component is an anti-P-selectin antibody/tag2 conjugate. The different second component is specific for activated platelets by specifically binding, for example, P-selectin, which is a protein expressed on activated platelets.
2. Incubate the blood sample for 30 seconds.
3. Apply the blood to a device which has two discrete zones on a solid phase comprising anti-tag1 antibody and anti-tag2 antibody.
4. Wash away unbound label.
5. Measure the amount of label (reporter molecule) at the first and second zones, which represents the degree of drug bound to the glycoprotein IIbIIIa and the degree of activated platelets, respectively.

Example 3

Method for Determining the Ratio of Hemoglobin A1-C to Hemoglobin

The following procedure can be followed by those skilled in the art to determine the ratio of hemoglobin A1-C to hemoglobin in a sample. The ratio of hemoglobin A1-C to hemoglobin can be determined using two different methods. Method A utilizes two components and Method B utilizes three components. Method B provides advantages when the concentration of the biological molecule that specifically binds the second component is greater than the concentration of the second component in a sample.

Method A
1. Prepare an aqueous biological sample. The sample can be a fluid sample extracted from the patient, a fluid sample circulating from the patient to a machine and back to the patient, or a tissue sample.
2. Contact the biological sample with the first and second components of the invention. The first component has specific binding affinity for both hemoglobin and hemoglobin A1-C and its concentration in the fluid sample is less that the total concentration of hemoglobin in the fluid sample. The second component is specific for hemoglobin A1-C and its concentration in the fluid sample can be greater than, equal to, or less than the concentration of the first component. If the first or second components are not attached to a solid support matrix, one of the components can be attached to a solid support at this step.
3. Wash the solid support with a suitable buffer, such as phosphate buffered saline.
4. Measure a signal from the signal generating (reporter) molecule preferably linked to the first component of the invention.
5. Extrapolate the ratio of hemoglobin A1-C to hemoglobin from a standard curve.

Method B
1. Prepare an aqueous biological sample. The sample can be a fluid sample extracted from the patient, a fluid sample circulating from the patient to a machine and back to the patient, or a tissue sample.
2. Contact the biological sample with the first, second, and third components of the invention. The first component has specific binding affinity for both hemoglobin and hemoglobin A1-C and its concentration in the fluid sample is less that the total concentration of hemoglobin in the fluid sample. The second component is specific for hemoglobin A1-C and its concentration in the fluid sample can be greater than, equal to, or less than the concentration of the first component. The third component has specific binding affinity for the complex comprising the second component and either hemoglobin or hemoglobin A1-C. The third component can be directly attached to a solid support or it can be free in solution and comprise a specific recognition moiety, such as biotin or a hemagglutinin tag, that binds to avidin or an anti-hemagglutinin antibody, respectively, attached to a solid support. The concentration of the third component is greater than the concentration of the second component.
3. Wash the solid support with a suitable buffer, such as phosphate buffered saline.
4. Measure a signal from the signal generating (reporter) molecule preferably linked to the first component of the invention.
5. Extrapolate the ratio of hemoglobin A1-C to hemoglobin from the standard curve.

Example 4

Method for Determining the Ratio of Oxidized Troponin I to Reduced Troponin I

The following procedure can be followed by those skilled in the art to determine the ratio of oxidized troponin I to reduced troponin I in a sample. The ratio of oxidized troponin I to reduced troponin I can be determined using two different methods. Method A utilizes two components and Method B utilizes three components. Method B provides advantages when the concentration of the biological molecule that specifically binds the second component is greater than the concentration of the second component in a sample.

Method A
1. Prepare a sample from a patient. The sample can be a fluid sample extracted from the patient, a fluid sample circulating from the patient to a machine and back to the patient, or a tissue sample.
2. Contact the biological sample with the first and second components of the invention. The first component has specific binding affinity for both oxidized and reduced troponin I and its concentration in the fluid is sample less that the total concentration of the troponin I in the fluid sample. The second component is specific for only oxidized or reduced troponin I and its concentration in the fluid sample can be greater than, equal to, or less than the concentration of the first component. If the first or second components are not attached to a solid support matrix, one of the components can be attached to a solid support at this step.
3. Wash the solid support with a suitable buffer, such as phosphate buffered saline.
4. Measure a signal from the signal generating (reporter) molecule preferably linked to the first component of the invention.
5. Extrapolate the ratio of oxidized troponin I to reduced troponin I from a standard curve.

Method B
1. Prepare an aqueous biological sample. The sample can be a fluid sample extracted from the patient, a fluid sample circulating from the patient to a machine and back to the patient, or a tissue sample.
2. Contact the biological sample with the first, second, and third components of the invention. The first component has specific binding affinity for both oxidized and reduced troponin I and its concentration in the fluid sample is less that the total concentration of troponin I in the fluid sample. The second component is specific for only oxidized or reduced troponin I and its concentration in the fluid sample can be greater than, equal to, or less than the concentration of the first component. The third component has specific binding affinity for the complex comprising the second component and either oxidized troponin I or reduced troponin I. The third component can be directly attached to a solid support or it can be free in solution and comprise a specific recognition moiety, such as biotin or a hemagglutinin tag, that binds to avidin or an anti-hemagglutinin antibody, respectively, attached to a solid support. The concentration of the third component is greater than the concentration of the second component.
3. Wash the solid support with a suitable buffer, such as phosphate buffered saline.
4. Measure a signal from the signal generating (reporter) molecule preferably linked to the first component of the invention.
5. Extrapolate the ratio of oxidized troponin I to reduced troponin I from the standard curve.

Example 5

Generation of a Standard Curve

The following protocol can be used to generate a standard curve to be used in the methods of the present invention.
1. Prepare dilutions of each biological molecule in a suitable buffer, such as phosphate buffered saline plasma, serum whole blood, or urine. Diluted solutions should be prepared in a wide range of concentrations of the biological molecules. This in vitro method can be utilized with simple buffers as the diluent or with elements from biological fluid samples. Alternatively, in vivo samples can be utilized for the generation of a standard curve, in which the ratio of the biological molecules has been predetermined by the slower methods existing in the art.
2. Add the first component, second component, and optionally, the third component of the invention to each diluted sample of biological molecule. The concentration of the first component is less than the concentration of the biological molecules. The concentration of the second component is greater than, equal to, or less than the concentration of the first component. The concentration of the third component, if utilized, is greater than the concentration of the second component.
3. If one or both of the components are not attached to a solid support already, link one of the components to a solid support using methods described herein.
4. Wash away unbound molecules. Washing can be accomplished by removing the reaction liquid from the solid support and washing the solid support with a suitable buffer, such as phosphate buffered saline.
5. Measure the signal from a signal-generating molecule preferably linked to the first component of the invention.

6. Plot the measured signal versus the predetermined ratio of the biological molecules for each sample.
7. Determine the mathematical function that best fits the data points in the plot. Mathematical functions can include a linear, exponential, or hyperbolic function.

Example 6

Determination of Normalization Factors

The following procedure can be used to determine normalization factors to be used when determining the ratio of related biological molecules when the first component does not bind with equal affinity to both biological molecules.

1. Attach a purified biological molecule to a solid support. Attach another biological molecule to be determined for the ratio to a solid support in a different vessel. For this example the biological molecules comprising the ratio are molecules A and B.
2. Contact each of the biological molecules bound to the solid supports with the first component of the invention.
3. Wash unbound material away from the solid support.
4. Determine the amount of the first component bound to A and determine the amount of the first component of bound to B. The amount of the first component can be determined by a reporter molecule linked to the first component itself or by binding the first component with a binding molecule linked to a reporter molecule.
6. Determine the normalization factor (NF) using the following expression:

$$NF=[A]/[B]$$

where [A] is the amount of A and where [B] is the amount of B, expressed in terms of concentration or in terms of signal units.

The normalization factor can be utilized as a multiplication factor for the relative bias of an antibody binding A vs. B.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms comprising, consisting essentially of and consisting of may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are within the following claims.

What is claimed is:

1. A method for determining a ratio corresponding to the amount of a first biological molecule in a solution compared to the amount of a second biological molecule in said solution, the method comprising:
    (a) contacting said solution with
        (i) a first component having a specific binding affinity for each of said first and said second biological molecules, wherein said first component binds only one of said first or said second biological molecules at a time; and
        (ii) a second component having a specific binding affinity that provides binding to said first biological molecule bound to said first component and that does not provide binding to said second biological molecule bound to said first component, wherein said second component binds to said first biological molecule bound to said first component, but does not bind to said second biological molecule bound to said first component; and
    (b) determining a signal from a complex comprising said first biological molecule, said first component, and said second component, and relating the amount of said signal to the ratio corresponding to the amount of said first biological molecule in said solution compared to the amount of said second biological molecule in said solution by correlating said signal to a standard signal corresponding to a known ratio of said first and second biological molecules.

2. The method of claim 1, further comprising contacting said solution with a third component having a specific binding affinity for each of a third biological molecule and a fourth biological molecule present in said solution, wherein said third component binds only one of said third or fourth biological molecules at a time.

3. The method of claim 2, further comprising contacting said solution with a fourth component having a specific binding affinity that provides binding to said third biological molecule bound to said third component and that does not provide binding to said fourth biological molecule bound to said third component, wherein said fourth component binds to said third biological molecule bound to said third component, but does not bind to said fourth biological molecule bound to said third component.

4. The method of claim 1, wherein at least one of said first or second components comprises an antibody.

5. The method of claim 1, wherein at least one of said first or second components comprises a specific recognition moiety.

6. The method of claim 1, wherein at least one of said first or second components comprises a linkage to a solid support.

7. The method of claim 1, wherein at least one of said first or second components comprises a reporter molecule.

8. The method of claim 1, wherein said second component has specific binding affinity for a complex comprising said first biological molecule and said first component.

9. The method of claim 1, wherein said first component comprises a binding moiety having specific binding affinity for each of said first and second biological molecules, wherein said first and second biological molecules bind to said first component in a ratio corresponding to the amount of said first biological molecule in said solution compared to the amount of said second biological molecule in said solution.

10. The method of claim 1, wherein said first component comprises:
  (a) a first binding moiety having specific binding affinity for said first biological molecule; and
  (b) a second binding moiety having specific binding affinity for said second biological molecule, wherein binding of one of said first or second biological molecules to its respective binding moiety excludes binding of the other biological molecule to its respective binding moiety.

11. The method of claim 9 or 10, wherein said first component comprises at least one antibody as a binding moiety.

12. The method of claim 1, wherein said first and second biological molecules are occupied receptor and free receptor, respectively.

13. The method of claim 1, wherein said biological molecules are hemoglobin and hemoglobin A1-C, respectively.

14. The method of claim 1, wherein said biological molecules are oxidized troponin I and reduced troponin I, respectively.

15. The method of claim 12, wherein said first component has specific binding affinity for both occupied receptor and free receptor, and wherein said second component has specific binding affinity for:
  (a) said occupied receptor;
  (b) said free receptor;
  (c) a complex comprising said occupied receptor and said first component; or
  (d) a complex comprising said fee receptor and said first component.

16. The method of claim 1, wherein said first component has specific binding affinity for both hemoglobin and hemoglobin A1-C, and wherein said second component has specific binding affinity for:
  (a) said hemoglobin;
  (b) said hemoglobin A1-C;
  (c) a complex comprising said hemoglobin and said first component; or
  (d) a complex comprising said hemoglobin A1-C and said first component.

17. The method of claim 1, wherein said first component has specific binding affinity for both oxidized troponin I and reduced troponin I, and wherein said second component has specific binding affinity for:
  (a) said oxidized troponin I;
  (b) said reduced troponin I;
  (c) a complex comprising said oxidized troponin I and said first component; or
  (d) a complex comprising said reduced troponin I and said first component.

18. The method of claim 1, further comprising the step of contacting said solution with a third component after step (a) and before step (b), wherein said third component has a specific binding affinity that provides binding to said first biological molecule bound to said second component and that does not provide binding to said first biological molecule bound to said first component, wherein said third component binds to said first biological molecule bound to said second component, but does not bind to said first biological molecule bound to said first component.

19. The method of claim 1, further comprising the step of removing molecules that are not bound to said complex comprising said first biological molecule, said first component, and said second component.

20. The method of claim 1, wherein said relating step comprises the step of comparing said amount of said complex comprising said first biological molecule, said first component, and said second component to a standard curve, wherein said standard curve provides a relationship between the amount of said complex and said ratio corresponding to the amount of said first biological molecule in said solution compared to the amount of said second biological molecule in said solution.

21. The method of claim 20, wherein said step of comparing said amount of said complex to said standard curve comprises comparing a signal generated from a reporter molecule to said standard curve.

22. A method for determining a ratio of biological molecules in a solution, the method comprising:
  (a) contacting said solution with
    (i) a first component having a specific binding affinity for each of a plurality of different biological molecules, wherein said first component binds only one of said plurality of different biological molecules at a time; and
    (ii) a second component having a specific binding affinity that provides binding to a first complex comprising a first member of said plurality of different biological molecules bound to said first component and that does not provide binding to complexes comprising members of said plurality of biological molecules bound to said first component other than said first member, wherein said second component binds to said first complex, but does not bind to complexes comprising members of said plurality of biological molecules bound to said first component other than said first member; and
  (b) determining a signal from a second complex comprising said first complex bound to said second component, and relating the amount of said signal to the ratio corresponding to the amount of said first member in said solution compared to the total amount of said plurality of different biological molecules other than said first member in said solution by correlating said signal to a standard signal corresponding to a known ratio of said first member compared to the total amount of said plurality of different biological molecules other than said first member.

23. The method of claim 22, wherein at least one of said first or second components comprises an antibody.

24. The method of claim 22, wherein at least one of said first or second components comprises a specific recognition moiety.

25. The method of claim 22, wherein at least one of said first or second components comprises a linkage to a solid support.

26. The method of claim 22, wherein at least one of said first or second components comprises a reporter molecule.

27. The method of claim 22, wherein said first member is selected from the group consisting of free glycoprotein IIbIIIa receptor, occupied glycoprotein IIbIIIa receptor, activated platelets and inactivated platelets.

28. The method of claim 1, wherein said amount of said signal is related to a ratio corresponding to the amount of free glycoprotein IIbIIIa receptor in said solution to the amount of occupied glycoprotein IIBIIIa receptor in said solution or is related to a ratio corresponding to the amount of activated platelets in said solution to the amount of inactive platelets in said solution.

* * * * *

UNITED STATES PATENT AND TRADEMARK OFFICE
CERTIFICATE OF CORRECTION

PATENT NO. : 6,670,196 B1  Page 1 of 1
DATED : December 30, 2003
INVENTOR(S) : Kenneth F. Buechler It is certified that error appears in the above-identified patent and that said Letters Patent is hereby corrected as shown below:

<u>Column 39,</u>
Line 31, replace "fee" with -- free --.

Signed and Sealed this

Twenty-fourth Day of February, 2004

JON W. DUDAS
*Acting Director of the United States Patent and Trademark Office*